(12) United States Patent
Nishiwaki et al.

(10) Patent No.: US 11,067,451 B2
(45) Date of Patent: *Jul. 20, 2021

(54) PHOTO-DETECTION SYSTEM COMPRISING PHOTO-DETECTION APPARATUS INCLUDING LIGHT-SHIELDING FILM, OPTICALLY-COUPLED LAYER, AND PHOTODETECTOR AND ARITHMETIC CIRCUIT

(71) Applicant: Panasonic Intellectual Property Management Co., Ltd., Osaka (JP)

(72) Inventors: Seiji Nishiwaki, Hyogo (JP); Kenji Narumi, Osaka (JP); Yasuhiko Adachi, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 347 days.

This patent is subject to a terminal disclaimer.

(21) Appl. No.: 15/828,573

(22) Filed: Dec. 1, 2017

(65) Prior Publication Data

US 2018/0164160 A1    Jun. 14, 2018

(30) Foreign Application Priority Data

Dec. 8, 2016 (JP) .............................. JP2016-238793

(51) Int. Cl.
*H01L 27/00* (2006.01)
*G01J 5/08* (2006.01)
(Continued)

(52) U.S. Cl.
CPC .......... *G01J 5/0871* (2013.01); *A61B 5/1455* (2013.01); *A61B 5/14552* (2013.01);
(Continued)

(58) Field of Classification Search
CPC .............. A61B 5/1455; A61B 5/14552; A61B 5/14553; G01B 9/02; G01B 9/02041;
(Continued)

(56) References Cited

U.S. PATENT DOCUMENTS 5,113,286 A    5/1992  Morrison
5,659,494 A *  8/1997  Chmielewski ........... H04N 5/21
                                                 348/E5.077
(Continued)

FOREIGN PATENT DOCUMENTS

JP    1-291478    11/1989
JP    2007-225453    9/2007
(Continued)

OTHER PUBLICATIONS

Max Born et al., "Principles of Optics", Tokai University Press, Dec. 20, 1980, pp. 478-485 (Partial Translation).
(Continued)

*Primary Examiner* — Georgia Y Epps
*Assistant Examiner* — Kevin Wyatt
(74) *Attorney, Agent, or Firm* — McDermott Will and Emery LLP

(57) ABSTRACT

A photo-detection system includes: a photo-detection apparatus including a light-shielding film, an optically-coupled layer, and a photodetector including first and second photo-detection cells; and an arithmetic circuit that generates, based on first signals and second signals, third signals each representing coherence of light having entered a position of each of the first and second photo-detection cells and generates at least one selected from the group consisting of an average value of the third signals, a standard deviation of the third signals, a ratio between the standard deviation and the average value, and a ratio between an average value of a first portion of the third signals based on light having
(Continued)

entered the positions of the first photo-detection cells and an average value of a second portion of the third signals based on light having entered the positions of the second photo-detection cells.

9 Claims, 29 Drawing Sheets

(51) Int. Cl.

| | |
|---|---|
| *G01B 9/02* | (2006.01) |
| *H01L 27/146* | (2006.01) |
| *G01J 1/04* | (2006.01) |
| *A61B 5/1455* | (2006.01) |
| *G01N 21/27* | (2006.01) |
| *G01N 21/17* | (2006.01) |
| *G01N 21/45* | (2006.01) |
| *G01J 9/00* | (2006.01) |
| *G01N 21/47* | (2006.01) |

(52) U.S. Cl.
CPC ............ *A61B 5/14553* (2013.01); *G01B 9/02* (2013.01); *G01B 9/02041* (2013.01); *G01B 9/02087* (2013.01); *G01J 1/04* (2013.01); *G01J 1/0411* (2013.01); *G01J 1/0414* (2013.01); *G01J 1/0422* (2013.01); *G01J 1/0437* (2013.01); *G01J 5/08* (2013.01); *G01J 9/00* (2013.01); *G01N 21/17* (2013.01); *G01N 21/27* (2013.01); *G01N 21/45* (2013.01); *H01L 27/146* (2013.01); *H01L 27/14627* (2013.01); *G01N 21/4795* (2013.01)

(58) Field of Classification Search
CPC ...... G01B 9/02087; G02B 5/18; G01N 21/45; G01N 21/17; G01N 21/27; H01L 27/14627; H01L 27/146; G01J 1/0414; G01J 1/0422; G01J 1/0437; G01J 1/04; G01J 1/0411; G01J 5/08; G01J 9/00; G01J 5/0871

USPC ....................................................... 250/208.1
See application file for complete search history.

(56) References Cited

U.S. PATENT DOCUMENTS

| | | | |
|---|---|---|---|
| 7,138,663 B2 | 11/2006 | Hoshuyama | |
| 8,224,109 B2* | 7/2012 | Bosco ..................... | G06K 9/40 |
| | | | 348/222.1 |
| 8,285,039 B2* | 10/2012 | Komiya .................. | G01J 3/508 |
| | | | 382/167 |
| 9,068,893 B2 | 6/2015 | Seo et al. | |
| 2011/0267487 A1 | 11/2011 | Yamagata et al. | |
| 2014/0078349 A1 | 3/2014 | Velichko et al. | |
| 2015/0168651 A1 | 6/2015 | Nishiwaki | |
| 2016/0360967 A1 | 12/2016 | Nishiwaki | |
| 2017/0070687 A1 | 3/2017 | Endsley | |
| 2017/0284863 A1 | 10/2017 | Nishiwaki et al. | |
| 2018/0167563 A1 | 6/2018 | Narumi et al. | |
| 2019/0080668 A1* | 3/2019 | Holenarsipur ........ | G01J 1/0474 |

FOREIGN PATENT DOCUMENTS

| | | |
|---|---|---|
| JP | 2014-138142 | 7/2014 |
| WO | 2014/199572 A1 | 12/2014 |

OTHER PUBLICATIONS

Goro Nishimura, "Prospects for Near-Infrared Spectroscopy—Possibilities of 1-μm Wavelength Region", The 14th Meeting of Japanese Society for Medical Near Infrared Spectroscopy, vol. 49, 24 Jul. 2009, pp. 139-145 (Whole sentence Translation).
Notice of Allowance issued in U.S. Appl. No. 15/825,041, dated Nov. 22, 2019.

\* cited by examiner

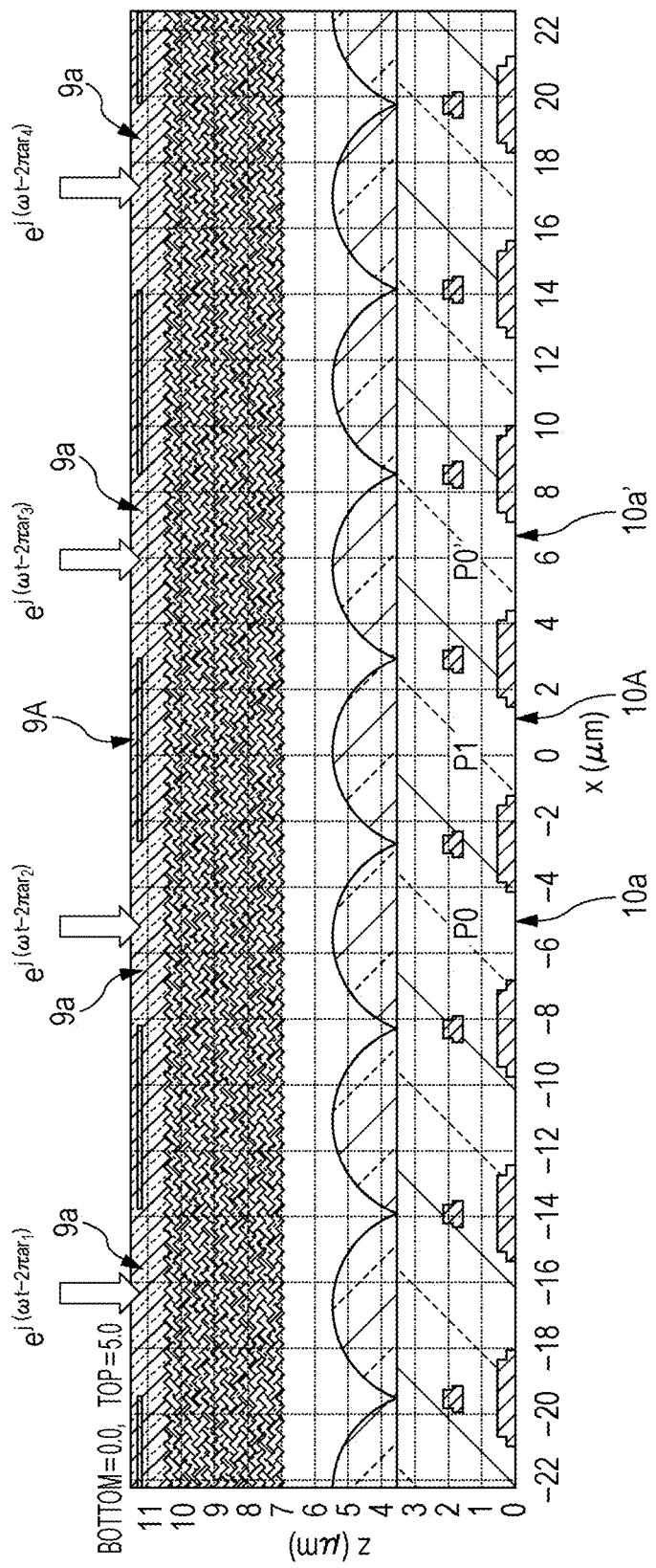

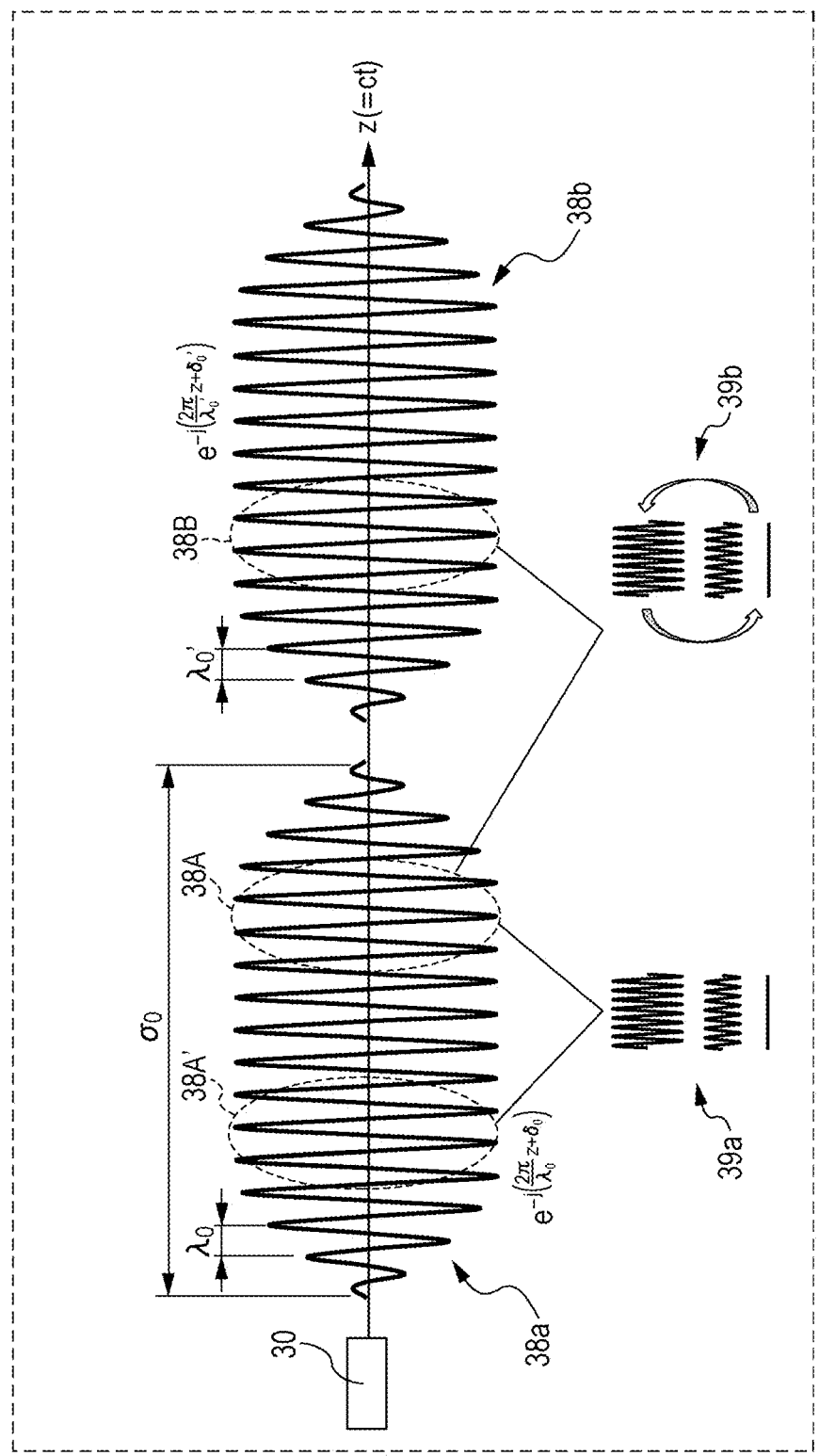

PHOTO-DETECTION SYSTEM COMPRISING PHOTO-DETECTION APPARATUS INCLUDING LIGHT-SHIELDING FILM, OPTICALLY-COUPLED LAYER, AND PHOTODETECTOR AND ARITHMETIC CIRCUIT

BACKGROUND

1. Technical Field

The present disclosure relates to a photo-detection system that acquires information regarding the optical characteristics of a subject by utilizing an interference phenomenon of light and to a light-emitting apparatus.

2. Description of the Related Art

Light is electromagnetic radiation that is characterized by characteristics such as polarization and coherence as well as wavelength and intensity. An example of a method for measuring a subject by utilizing the coherence, among other characteristics, of light is a method disclosed in Principles of Optics (Tokai University Press, p. 482, M. Born et al) that involves the use of a Michelson's interferometer.

SUMMARY

In one general aspect, the techniques disclosed here feature a photo-detection system including a photo-detection apparatus and an arithmetic circuit. The photo-detection apparatus includes a light-shielding film including light-transmitting regions and light-shielding regions, the light-transmitting regions and the light-shielding regions being alternately arranged in at least a first direction within a plane, an optically-coupled layer facing the light-shielding film, the optically-coupled layer including a grating which generates a propagating light that propagates in the first direction and a transmitting light that transmits the optically-coupled layer when incident light of a predetermined wavelength enters light-transmitting regions, and a photodetector having an imaging area, the photodetector including first photo-detection cells and second photo-detection cells, the first photo-detection cells and the second photo-detection cells being arranged on the imaging area, each of the first photo-detection cells corresponding to at least one of the light-transmitting regions, each of the second photo-detection cells corresponding to at least one of the light-shielding regions. The arithmetic circuit generates, based on first signals that are obtained from the first photo-detection cells and second signals that are obtained from the second photo-detection cells, third signals each representing coherence of light having entered a position of each of the first and second photo-detection cells. The arithmetic circuit generates at least one selected from the group consisting of an average value of the third signals, a standard deviation of the third signals, a ratio between the standard deviation and the average value, and a ratio between an average value of a first portion of the third signals and an average value of a second portion of the third signals in positions of at least a part of the first photo-detection cells and the second photo-detection cells that are included in a region of the imaging plane. The first portion of the third signals is based on light having entered the positions of the first photo-detection cells, and the second portion of the third signals is based on light having entered the positions of the second photo-detection cells.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6A is a cross-sectional view showing a positional relationship between incident light on four light-transmitting regions in the example of discussion and three photodetectors located therebelow;

FIG. 17 is a diagram for explaining an interference phenomenon of light;

DETAILED DESCRIPTION

Underlying Knowledge Forming Basis of the Present Disclosure

Prior to a description of an embodiment of the present disclosure, results of detailed discussion on conventional methods for measuring the coherence or phase of light are explained.

Figure 16A:
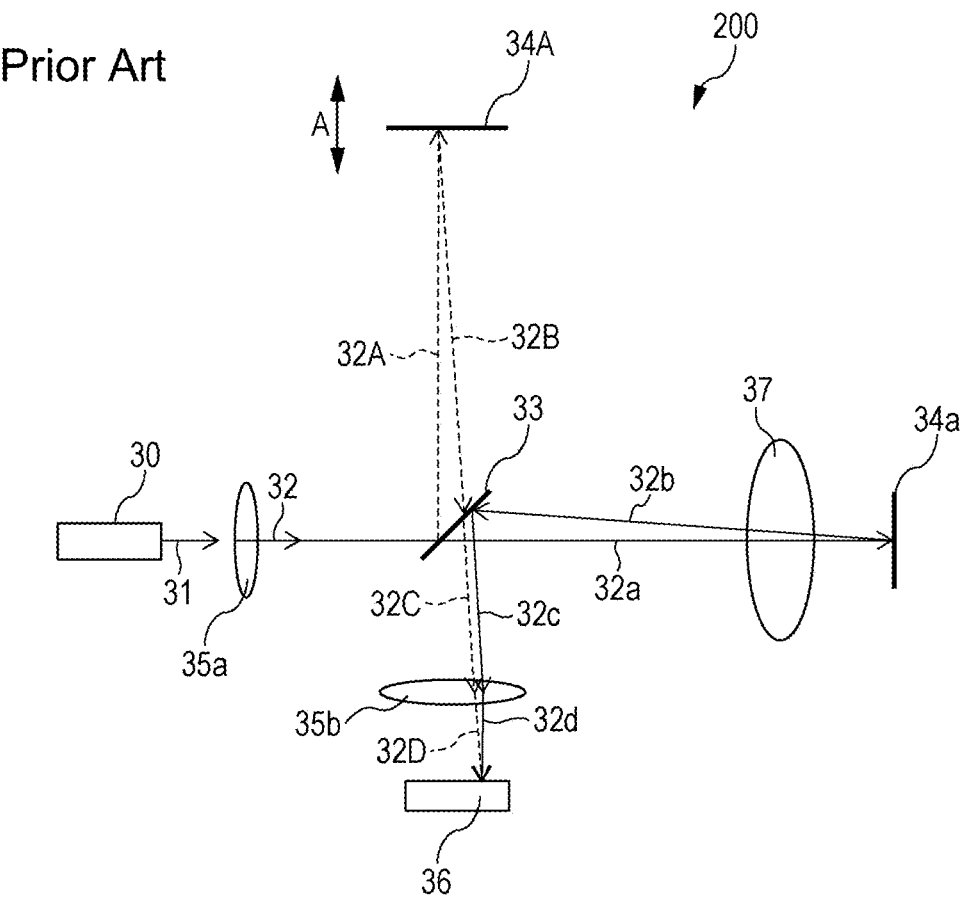
FIG. 16A is a diagram schematically showing a configuration of a Michaelson's interferometer according to a first conventional example.

FIG. 16A is a diagram schematically showing a configuration of a Michelson's interferometer 200 according to a first conventional example. As shown in FIG. 16A, light 31 emitted from a light source 30 is condensed by a first lens optical system 35a to turn into parallel light 32. It should be noted that FIG. 16A shows only the optical axis of the parallel light 32. Light 32a, which is a portion of this parallel light 32, is transmitted by a semitransparent mirror 33 and travels toward a first reflecting mirror 34a. Light 32b reflected from the first reflecting mirror 34a is further reflected by the semitransparent mirror 33 as light 32c that travels toward a second lens optical system 35b. The light 32c passes through the second lens optical system 35b and falls as light 32d on a photodetector 36 located on a focal plane of the second lens optical system 35b. Meanwhile, light 32A, which is another portion of the parallel light 32, is reflected by the semitransparent mirror 33 and travels toward a second reflecting mirror 34A. Light 32B reflected from the second reflecting mirror 34A travels toward the semitransparent mirror 33, is transmitted by the semitransparent mirror 33, and travels as light 32C toward the second lens optical system 35b. The light 32C passes through the second lens optical system 35b and falls as light 32D on the photodetector 36 in such a form as to overlap the light 32d. The photodetector 36 detects light that is generated by interference between the light 32d and the light 32D. The second reflecting mirror 34A is configured to change its position along the direction (arrow A) of the normal to the plane of reflection. Along with a change in position of the second reflecting mirror 34A, the phase of the light 32D relative to the light 32d changes.

Figure 16B:
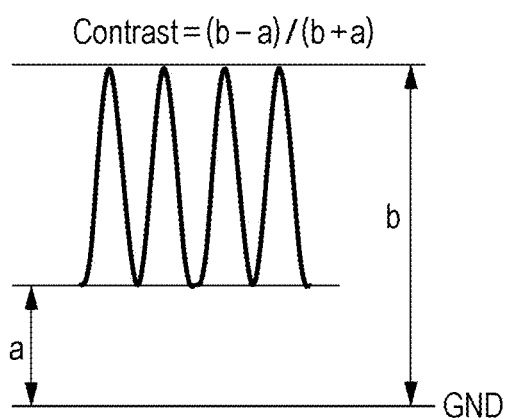
FIG. 16B is a diagram schematically showing an example of a time change in an electrical signal representing the intensity of light as detected by a photodetector.

FIG. 16B is a diagram schematically showing an example of a time change in an electrical signal representing the intensity of light as detected by the photodetector 36. FIG.

16B shows a method for evaluating the coherence and phase of light with the Michelson's interferometer 200. In FIG. 16B, the vertical axis represents the strength of a signal that is outputted from the photodetector 36, and the horizontal axis represents time. As shown in FIG. 16B, changing the position of the second reflecting mirror 34A over time causes the signal strength to change within a range of a to b. Note here that the value of (b−a)/(b+a) is called "contrast in interference". The degrees of coherence of light 31 is defined according to the value of contrast.

Even in a case where the second reflecting mirror 34A is fixed and a transparent subject 37 is placed between the semitransparent mirror 33 and the first reflecting mirror 34a, the same principles hold as those which hold in a case where the position of the second reflecting mirror 34A is changed. That is, in the strength of a signal that is outputted from the photodetector 36, such as an image sensor, a difference in strength in conformance with the shape of the subject 37 appears as a spatial distribution to form so-called interference fringes. The shape or phase information of the subject 37 can be measured by measuring the shape of or the intervals between the interference fringes.

In order to measure the spatial distribution of the interference fringes at once, the photodetector 36 may be an aggregate of detectors each of which detects an amount of light that falls on that detector. Individual photodetectors constituting the aggregate of detectors are also called "pixels".

FIG. 17 is a diagram for explaining an interference phenomenon of light. FIG. 17 schematically shows the appearance at a point in time $t_0$ of light that is emitted from the light source 30 and propagates in a Z direction. As shown in FIG. 17, a plurality of wave packets such as wave packets 38a and 38b are emitted one after another from the light source 30. The length $\sigma_0$ of a wave packet is called "coherence length". One wave packet includes a series of waves that are uniform in wavelength. Different wave packets have no phase correlation with each other. For example, $\delta_0 \neq \delta_0'$, where $\delta_0$ is the phase of the wave packet 38a and $\delta_0'$ is the phase of the wave packet 38b. Different wave packets may differ in wavelength from each other. For example, $\lambda_0 \neq \lambda_0'$, where $\lambda_0$ is the wavelength of the wave packet 38a and $\lambda_0'$ is the wavelength of the wave packet 38b.

First, a case is described where interference between portions 38A and 38A' of the wave packets 38a shown in FIG. 17 is caused by adjusting the position of the second reflecting mirror 34A in the configuration shown in FIG. 16A. Waves in the portion 38A and waves in the portion 38A' are equal in wavelength to each other and are also temporally stable in phase difference between waves. Therefore, the brightness and darkness of light after interference (amplitude of interfering light) are also temporally stable. That is, as shown in the lower left part of FIG. 17, interfering light 39a appears bright (in the upper row of the lower left part) or appears dark (in the lower row of the lower left part) according to the amount of phase difference (i.e. the change in position of the second reflecting mirror 34A). This state is called "coherent".

Next, a case is described where interference between the portion 38A of the wave packet 38a and a portion 38B of the wave packet 38b is caused. In this case, there is no guarantee that the waves in the portion 38A and the waves in the portion 38B are equal in wavelength to each other, and the phase difference between these two types of waves also randomly changes over time. As a result, the brightness and darkness of light after interference (amplitude of interfering light) randomly change over time. These changes occur, for example, at speeds of the order of femtoseconds. Therefore, as shown in the lower right part of FIG. 17, interfering light 39b repeats its brightness and darkness alternately at high speeds and only appears to the human eye to be of average brightness. This state is called "incoherent". Laser light has a long wave packet and a coherence length of approximately several meters of several hundreds of meters and, as such, is a typical example of coherent light. Meanwhile, sunlight has a short wave packet and a coherence length of approximately 1 μm and, as such, is a typical example of incoherent light. In the case of interference of light in such a configuration as that shown in FIG. 16A, use of light of long coherence length, such as laser light, gives a high probability of interference within the same wave packet. As a result, the contrast improves to approximately 1. Meanwhile, use of light of short coherence length, such as sunlight, gives a high probability of interference between different wave packets (i.e. a low probability of interference between the same wave packets). As a result, the contrast lowers to approximately 0.

Figure 18A:
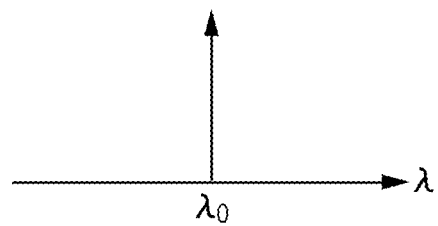
FIG. 18A shows light whose spread of wavelength centered at the wavelength $\lambda_0$ is zero.
Figure 18B:
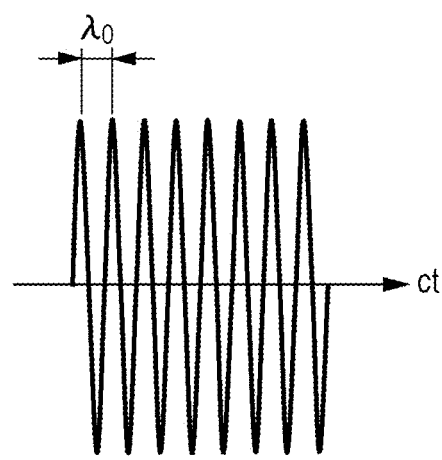
FIG. 18B shows that the coherence length reaches an infinite value.
Figure 18C:
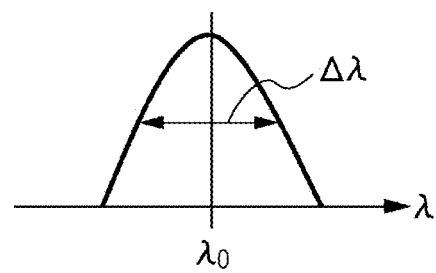
FIG. 18C shows light whose spread of wavelength (FWHM) centered at the wavelength $\lambda_0$ is $\Delta\lambda$.
Figure 18D:
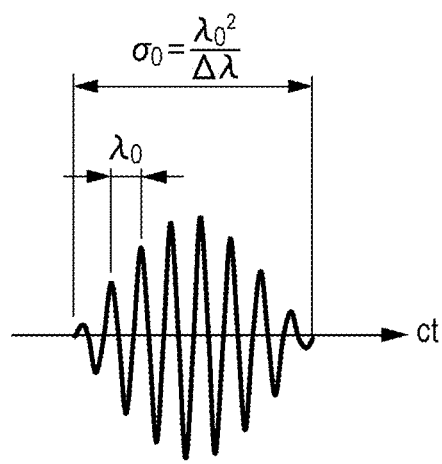
FIG. 18D shows that the coherence length $\sigma_0$ becomes $\lambda_0^2/\Delta\lambda$.

FIGS. 18A to 18E show a relationship between the spread of wavelength (longitudinal mode width) and coherence length of light with a center wavelength $\lambda_0$. FIG. 18A shows light whose spread of wavelength centered at the wavelength $\lambda_0$ is zero. In this case, as shown in FIG. 18B, the coherence length reaches an infinite value. FIG. 18C shows light whose spread of wavelength (FWHM) centered at the wavelength $\lambda_0$ is $\Delta\lambda$. In this case, as shown in FIG. 18D, the coherence length $\sigma_0$ becomes $\lambda_0^2/\Delta\lambda$. The longitudinal mode width and the coherence length are in a relationship of Fourier transform. This is called "Wiener-Khinchin theorem". This theorem can be explained as follows.

Figure 18E:
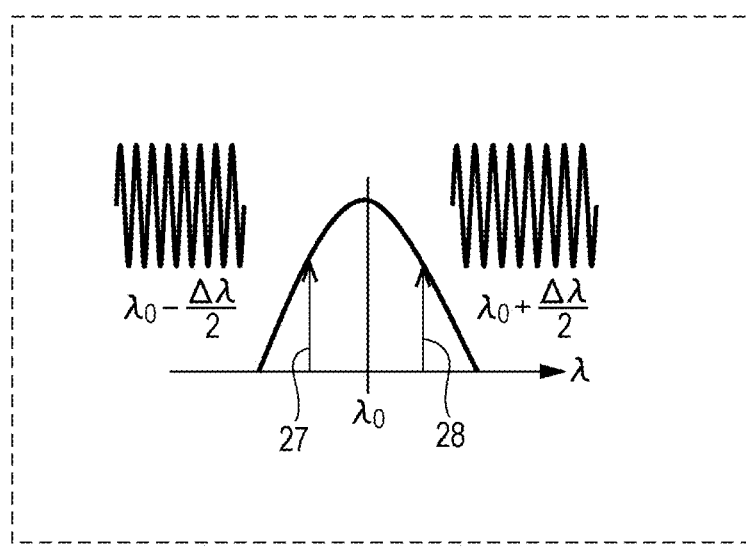
FIG. 18E shows that light whose center wavelength is $\lambda_0$ and whose spread of wavelength is $\Delta\lambda$ can be expressed by substitution with two rays of light with wavelengths of $\lambda_0-\Delta\lambda/2$ and $\lambda_0+\Delta\lambda/2$.

FIG. 18E shows that light whose center wavelength is $\lambda_0$ and whose spread of wavelength is $\Delta\lambda$ can be expressed by substitution with two rays of light 27 and 28 with wavelengths of $\lambda_0-\Delta\lambda/2$ and $\lambda_0+\Delta\lambda/2$. The period of a beat that is generated by interference between the light 27 and the light 28 is $\lambda_0^2/\Delta\lambda$. The wavelength of a carrier wave is the average value $\lambda_0$ of the wavelengths of the light 27 and the light 28. An oscillatory waveform of light is uniformly continuous within the period of the beat. Meanwhile, an oscillatory waveform of light of a different period loses its continuity, thus also losing its phase correlation. That is, the period $\lambda_0^2/\Delta\lambda$ of the beat is equivalent to the coherence length. The reason why sunlight is incoherent is that sunlight is large in spread of wavelength (longitudinal mode width) $\Delta\lambda$. Assuming that the center wavelength $\lambda_0$ is 550 nm and the spread of wavelength $\Delta\lambda$ is 300 nm, the coherence length $\sigma_0$ is given as $\lambda_0^2/\Delta\lambda=1.0$ μm.

Next, a photo-detection system disclosed in "Near-infrared Spectroscopy in a 1-μm Wavelength Region: Current and Future" (14th Annual Meeting of Japanese Society for Medical Near Infrared Spectroscopy, p. 139-144, Goro Nishimura) is described as a second conventional example. The photo-detection system according to the second conventional example measures an intensity distribution of light by propagation distance of light.

Figure 19A:
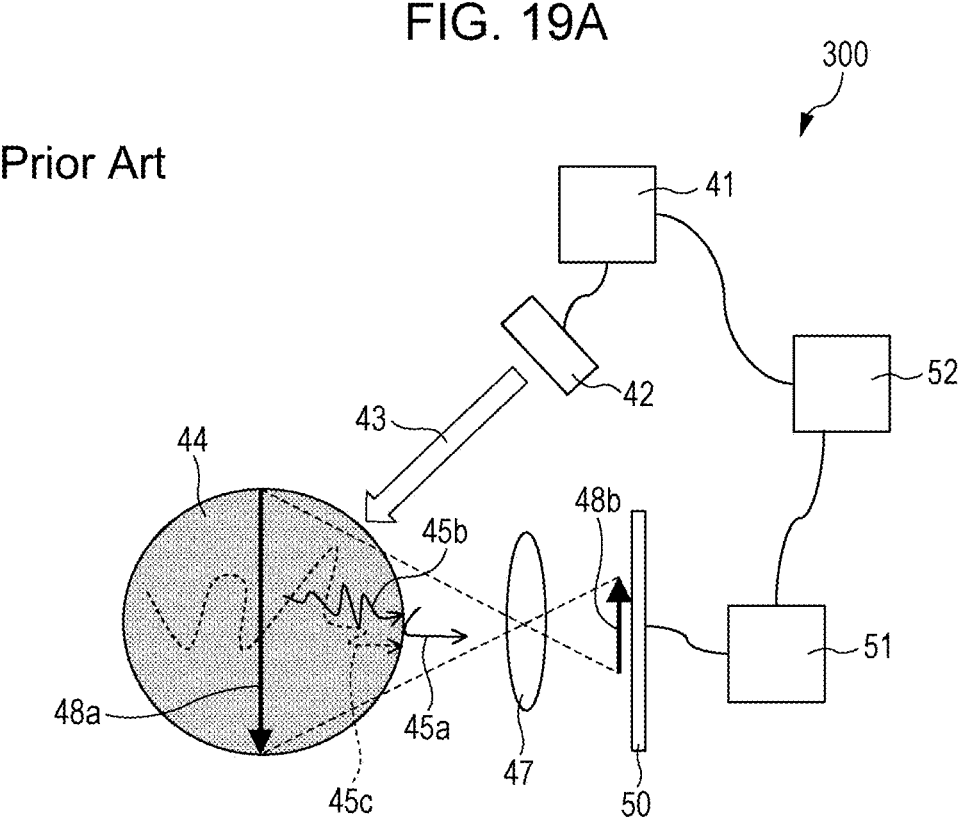
FIG. 19A is a schematic cross-sectional view of a photo-detection system according to a second conventional example.

FIG. 19A is a schematic cross-sectional view of a photo-detection system 300 according to the second conventional example. A light source 42 emits laser light. As shown in FIG. 19A, light 43 of a wavelength $\lambda_0$ emitted from the light source 42 is applied to a subject 44. As a result, scattering rays of light 45a, 45b, and 45c generated on a surface of or within the subject 44 are condensed by the lens optical system 47 to form an image 48b in an image surface position of the lens optical system 47. Present in correspondence with the image 48b is a substantial object 48a on an object side of the lens. Disposed in the image surface position is a photodetector 50. The photodetector 50 is an aggregate of detectors (i.e. pixels) each of which detects an amount of light that falls on that pixel. Emission of light from the light source 42 is controlled by a controller 41. An amount of light detected by the photodetector 50 is processed as a detected signal by an arithmetic circuit 51. The controller 41 and the arithmetic circuit 51 are controlled en bloc by a computer 52.

Figure 19B:
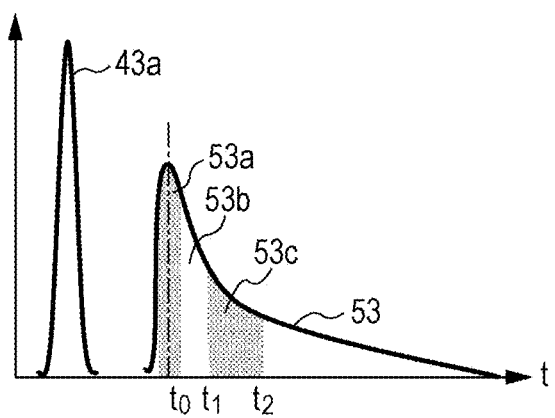
FIG. 19B is an explanatory diagram showing a relationship between the oscillation of a light source in the photo-detection system shown in FIG. 19A and a detected signal from a photodetector.

FIG. 19B is an explanatory diagram showing a relationship between the oscillation of the light source 42 in the photo-detection system 300 shown in FIG. 19A and a detected signal from the photodetector 50. In FIG. 19B, the vertical axis represents the oscillation intensity of the light source 42 or the detection intensity of the photodetector 50, and the horizontal axis represents elapsed time. The light source 42 generates a pulse 43a under the control of the controller 41. Light 43 based on this pulse 43a is scattered within the subject 44, received by the photodetector 50, and detected as a signal 53. The signal 53 is wider in time width than the original pulse 43a under the influence of variations in optical path length due to the scattering. A leading output 53a of the signal 53 is a signal component based on light 45a reflected on the surface of the subject 44. An output 53b during a period from time $t_0$ to time $t_1$ after the output 53a is a signal component based on light 45b that scatters a short distance within the subject 44. An output 53c during a period from time $t_1$ to time $t_2$ after the output 53b is a signal component based on light 45c that scatters a long distance. Control by the computer 52 allows the arithmetic circuit 51 to time-divide the detected signal 53, so that the outputs 53a, 53b, and 53c can be separately detected. The light passes through the subject 44 from a shallow side of the subject 44 to a deep side of the subject 44 in the order of the outputs 53a, 53b, and 53c. Therefore, information of different depths can be separately analyzed.

According to the inventor's discussion, the rays of light 32B and 32C from the second reflecting mirror 34A are needed to measure a degree of coherence or a phase by using the Michelson's interferometer 200 according to the first conventional example. Further, the presence of an interfering light path in a predetermined space increases susceptibility to a change (e.g. air convection or vibration) in ambient environment.

Meanwhile, according to the inventor's discussion, the photo-detection system 300 according to the second conventional example is limited in time-division width. Therefore, it is difficult to ensure sufficient depth resolution in performing measurements. For example, assuming the time-division width is 300 ps, the depth resolution is approximately 90 mm. For this reason, the photo-detection system 300 according to the second conventional example is not suited for diagnosing or inspecting a target having a comparatively small structure, such as a living organism.

Next, prior to a description of an embodiment of the present disclosure, an example of discussion, i.e. an embodiment that the inventor discussed to address the problems of the conventional examples, is described.

Example of Discussion

Figure 1A:
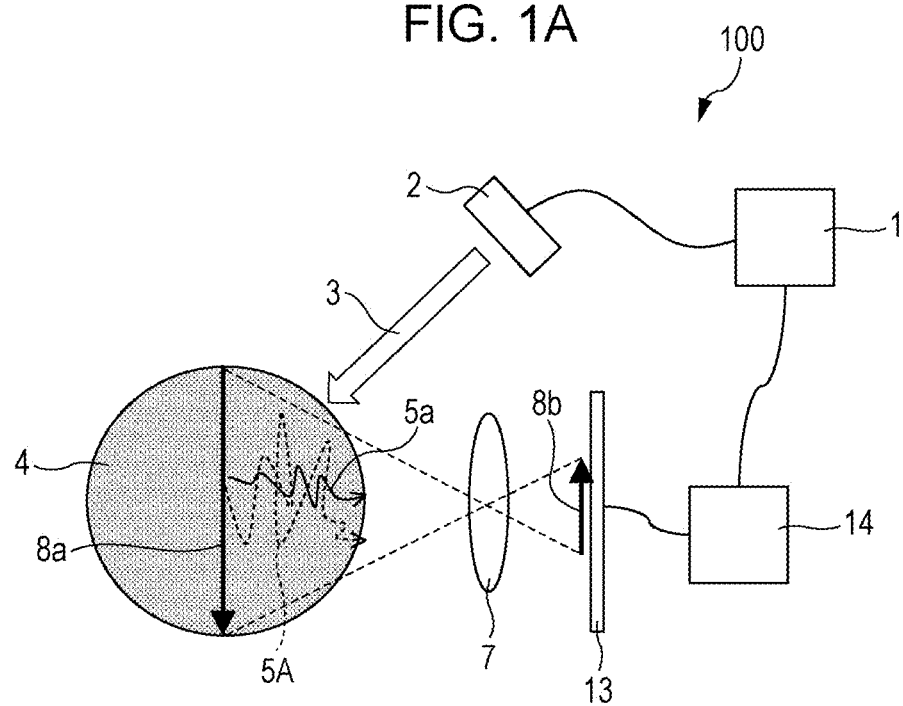
FIG. 1A is a schematic view of a photo-detection system according to an example of discussion.

FIG. 1A is a schematic view of a photo-detection system 100 according to an example of discussion. The photo-detection system 100 includes a light source 2, a lens optical system 7, a photo-detection apparatus 13, a control circuit 1, and an arithmetic circuit 14.

The light source 2 irradiates a subject 4 with light 3 of a certain coherence length. For example, the light source 2 may be a laser light source that emits laser light, which is a typical example of coherent light. The light source 2 may continuously emit light of constant intensity or may emit single pulsed light. The light source 2 may emit light of any wavelength. However, in a case where the subject 4 is a living organism, the wavelength of the light source 2 may be set, for example, at approximately 650 nm or longer and approximately 950 nm or shorter. This wavelength range is included in the wavelength range of red to near-infrared radiation. It is assumed herein that infrared radiation and ultraviolet radiation as well as visible light are encompassed in the concept of "light".

The lens optical system 7 is for example a condensing lens and condenses scattering rays 5a and 5A of light generated on a surface of or within the subject 4 by the light source 2 irradiating the subject 4 with light. The light thus condensed forms an image 8b in an image surface position of the lens optical system 7. Present in correspondence with the image 8b is a substantial object 8a on an object side of the lens optical system 7. In the example shown in FIG. 1A, the lens optical system 7 includes one lens. The lens optical system 7 may be an aggregate of lenses.

The photo-detection apparatus 13 is disposed in the image surface position of the lens optical system 7. The photo-detection apparatus 13 detects the scattering rays of light 5a and 5A condensed by the lens optical system 7. A structure of the photo-detection apparatus 13 will be described in detail later.

The arithmetic circuit 14 performs arithmetic processing on signals detected by the photo-detection apparatus 13. The arithmetic circuit 14 may be an image processing circuit such as a digital signal processor (DSP).

The control circuit 1 executes a program recorded, for example, in a memory and thereby controls at least one of the following: the detection of light by the photo-detection apparatus 13, the arithmetic processing that is performed by the arithmetic circuit 14, the amount of light that is emitted by the light source 2, the timing of lighting of the light source 2, the duration of continuous lighting of the light source 2, the emission wavelength of the light source 2, the coherence length of the light source 2, and the like. The control circuit 1 may be an integrated circuit such as a central processing unit (CPU) or a microcomputer. The control circuit 1 and the arithmetic circuit 14 may be realized by one integrated circuit.

It should be noted that the photo-detection system 100 may include a display (not illustrated) that displays the results of arithmetic processing performed by the arithmetic circuit 14.

Figure 1B:
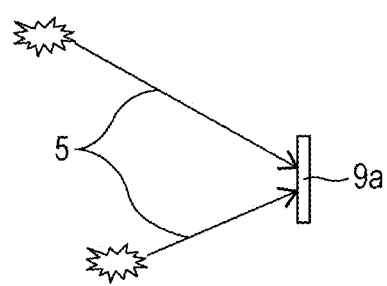
FIG. 1B shows the appearance of scattering light falling on one light-transmitting region of a photo-detection apparatus.

FIG. 1B shows the appearance of scattering light 5 falling on one light-transmitting region 9a of the photo-detection apparatus 13. The subject 4 is a scattering body. A ray of light propagating through the subject 4 is attenuated at an attenuation coefficient $\mu_a$ and repeats scattering at a scattering coefficient $\mu_s$.

Figure 2A:
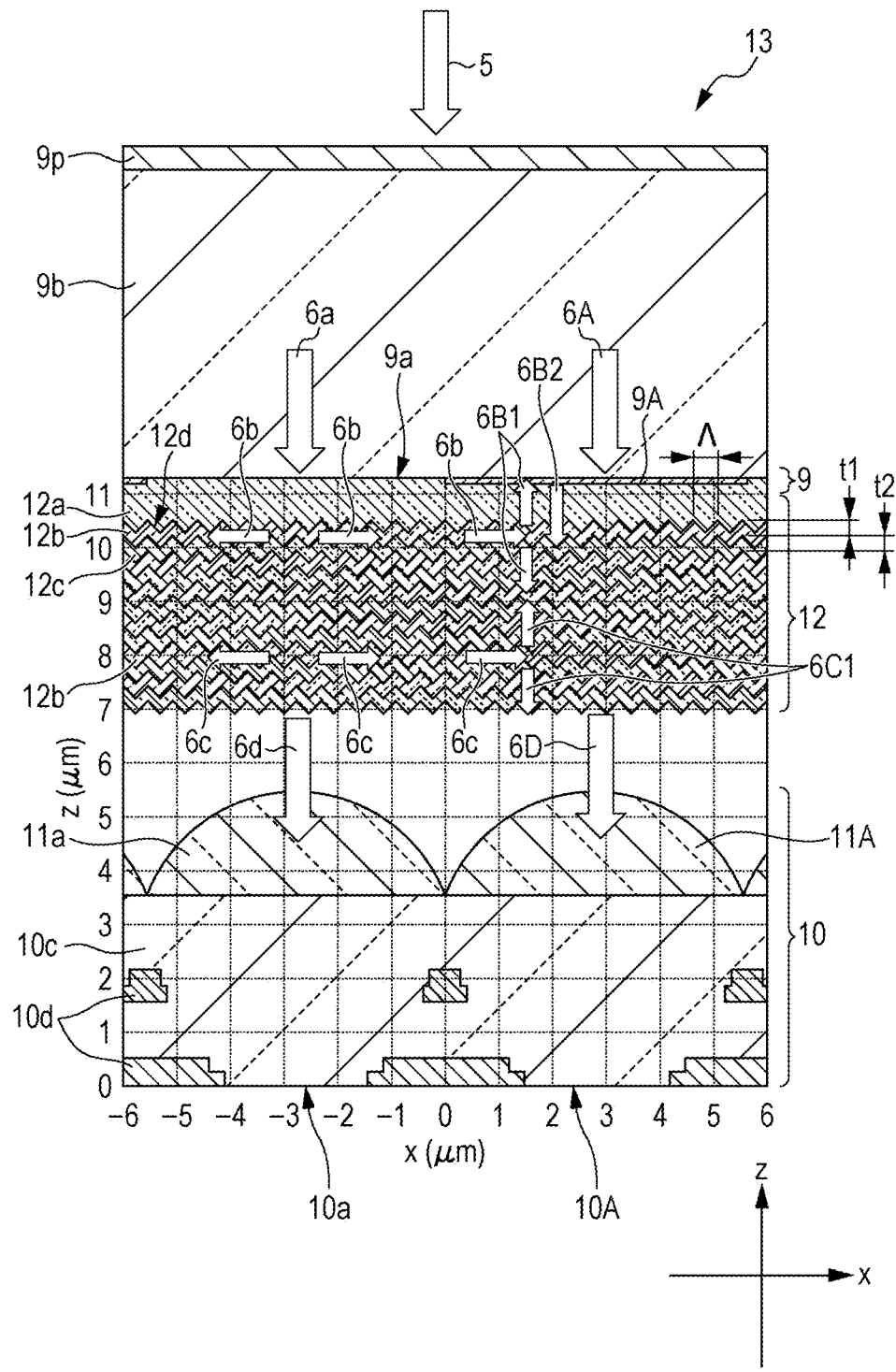
FIG. 2A is a cross-sectional view of the photo-detection apparatus as taken along a plane extending along a direction of incidence of light.
Figure 2B:
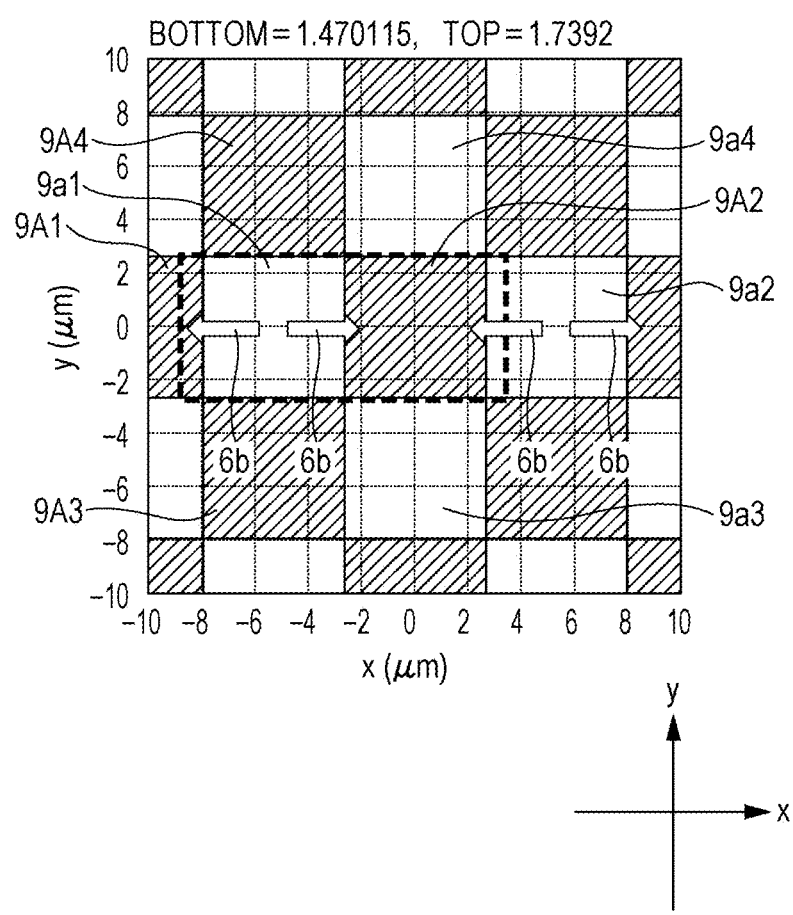
FIG. 2B is a plan view of the photo-detection apparatus as looked at from a side thereof on which light falls.

FIG. 2A is a cross-sectional view of the photo-detection apparatus 13 as taken along a plane extending along a direction of incidence of light. FIG. 2B is a plan view of the photo-detection apparatus 13 as looked at from a side thereof on which light falls (i.e. a plan view taken along an XY plane including the after-mentioned light-shielding film 9). FIG. 2A shows a cross-section that is parallel to an XZ plane including a region surrounded by dashed lines of FIG. 2B. As shown in FIG. 2B, assuming that the cross-sectional structure shown in FIG. 2A is one unit structure, these unit structures are periodically arranged in the XY plane. It should be noted, for convenience of explanation, FIGS. 2A and 2B show three orthogonal axes (namely, an X axis, a Y axis, and a Z axis). The same coordinate axes apply to other drawings.

The photo-detection apparatus 13 includes a photodetector 10, an optically-coupled layer 12, and a light-shielding film 9 in this order. In the example shown in FIG. 2A, the photodetector 10, the optically-coupled layer 12, and the light-shielding film 9 are stacked in a Z direction. In the example shown in FIG. 2A, the photo-detection apparatus 13 includes a transparent substrate 9b and a bandpass filter 9p in this order on top of the light-shielding film 9. The photo-detection apparatus 13 has an "imaging area" on which a plurality of pixels are arranged.

The photodetector 10 includes first pixels 10a and second pixels 10A in an in-plane direction (in the XY plane) of the photodetector 10. The first pixels 10a are first photo-detection cells, and the second pixels 10A are second photo-detection cells. The photodetector 10 includes a photoreceptor formed by microlenses 11a and 11A, a transparent film 10c, metal films 10d such as wires, and a Si or organic film, and the like, starting from the side on which light falls. The areas in the photoreceptor located in gaps in the metal films 10d are equivalent to the pixels 10a and 10A. The plurality of microlenses 11a and 11A are disposed so that one microlens faces one pixel. Light condensed by the microlenses 11a and 11A and entering the gaps in the metal films 10d is detected by the first pixels 10a and the second pixels 10A, respectively.

The optically-coupled layer 12 is disposed on top of the photodetector 10 and includes a first transparent layer 12c, a second transparent layer 12b, and a third transparent layer 12a in this order in a direction perpendicular to the surface of the photodetector 10 (i.e. a Z-axis direction). The first transparent layer 12c is a first low-refractive-index layer. The second transparent layer 12b is a first high-refractive-index layer. The third transparent layer 12a is a third low-refractive-index layer. The first transparent layer 12c and the third transparent layer 12a may be formed, for example, SiO$_2$ or the like. The second transparent layer 12b is formed, for example, by Ta$_2$O$_5$ or the like.

The second transparent layer 12b is higher in refractive index than the first transparent layer 12c and the third transparent layer 12a. The optically-coupled layer 12 may include a structure in which the second transparent layer 12b and the first transparent layer 12c are further repeated in this order. FIG. 2A shows a structure in which the second transparent layer 12b and the first transparent layer 12c are repeated a total of six times. The second transparent layer 12b is sandwiched between the first transparent layer 12c and the third transparent layer 12a. Therefore, the second transparent layer 12b functions as a waveguide layer. Gratings 12d, which are linear gratings of pitches Λ, are formed all over the interfaces between the second transparent layer 12b and the first transparent layer 12c and between the second transparent layer 12b and the third transparent layer 12a. The grating vector of each of the gratings 12d is parallel to the X axis in the in-plane direction (XY plane) of the optically-coupled layer 12. The XZ cross-sectional shape of the grating 12d is sequentially transferred onto the second transparent layer 12b and the first transparent layer 12c on which the grating 12d is stacked. In a case where the deposition of the second transparent layer 12b and the first transparent layer 12c is highly oriented in the direction in which they are stacked, shape transferability is easily maintained by forming the XZ cross-section of the grating 12d into an S or V shape.

It should be noted that the grating 12d needs only be included in a part of at least the second transparent layer 12b. The inclusion of the grating 12d in the second transparent layer 12b allows incident light to be coupled to guided light, i.e. light that propagates through the second transparent layer 12b.

It is preferable that a space between the optically-coupled layer 12 and the photodetector 10 be as narrow as possible. The optically-coupled layer 12 and the photodetector 10 may be in intimate contact with each other. The space between the optically-coupled layer 12 and the photodetector 10 (including a space in which the microlenses 11a and 11A are arranged) may be filled with a transparent medium such as an adhesive. In a case where the space is filled with the transparent medium, the microlenses 11a and 11A are made of a material having a greater refractive index than the transparent medium with which the space is filled, in order that the microlenses 11a and 11A bring about a lens effect.

The light-shielding film 9 has a structure in which a plurality of light-shielding regions 9A and a plurality of light-transmitting regions 9a are two-dimensionally arranged. In the example shown in FIG. 2A, the light-shielding regions 9A and the light-transmitting regions 9a are formed by patterning, on the after-mentioned transparent substrate 9b, a metal reflecting film formed, for example, by aluminum (Al) or the like.

The light-transmitting regions 9a in FIG. 2A correspond to light-transmitting regions 9a1, 9a2, 9a3, and 9a4 and the like in FIG. 2B. The light-shielding regions 9A in FIG. 2A correspond to light-shielding regions 9A1, 9A2, 9A3, and 9A4 and the like in FIG. 2B. That is, the light-shielding film 9 has the plurality of light-shielding regions 9A and the plurality of light-transmitting regions 9a arranged in an in-plane direction (in the XY plane) of the light-shielding film 9. The plurality of light-shielding regions 9A face the plurality of second pixels 10A, respectively. The plurality of light-transmitting regions 9a face the plurality of first pixels 10a, respectively. An aggregate of first pixels 10a is herein sometimes referred to as "first pixel group", and an aggregate of second pixels 10A is herein sometimes referred to as "second pixel group".

In the present disclosure, each of the first pixels 10a faces one of the light-transmitting regions 9a. Similarly, each of the second pixels 10A faces one of the light-shielding regions 9A.

It should be noted that two or more first pixels 10a may face one light-transmitting region. Similarly, two or more second pixels 10A may face one light-shielding region. The present disclosure also encompasses such an embodiment.

In the example shown in FIG. 2B, the plurality of light-shielding regions 9A1, 9A2, 9A3, and 9A4 form a checkered pattern. These light-shielding regions 9A1, 9A2, 9A3, and 9A4 may form a pattern other than the checkered pattern.

The transparent substrate 9b is disposed on a side of the light-shielding film 9 on which light falls. The transparent substrate 9b may be formed by a material such as SiO$_2$. The bandpass filter 9p is disposed on the side of the transparent substrate 9b on which light falls. The bandpass filter 9p selectively transmits only a portion of incident light 5 near the wavelength $\lambda_0$.

The light 5 falling on the photo-detection apparatus 13 travels through the bandpass filter 9p and the transparent substrate 9b as rays of light 6A and 6a that reach the light-shielding regions 9A, which are provided with the reflecting film, and the light-transmitting regions 9a, from which the reflecting film has been removed, respectively. The light 6A is blocked by the light-shielding regions 9A.

The light 6a is transmitted by the light-transmitting regions 9a and falls on the optically-coupled layer 12. The light 6a having fallen on the optically-coupled layer 12 travels through the third transparent layer 12a and falls on the second transparent layer 12b. The gratings 12d are formed at the interfaces on the top and bottom of the second transparent layer 12b. If Eq. (1) below is satisfied, guided light 6b is generated.

$$\sin\theta = N - \lambda_0/\Lambda \qquad \text{Eq. (1)}$$

Note here that N is the effective refractive index of the guided light 6b. θ is the angle of incidence with respect to the normal to the plane of incidence (XY plane). In FIG. 2A, light is incident perpendicularly to the plane of incidence (θ=0°). In this case, the guided light 6b propagates in an X direction in the XY plane. That is, light having traveled through the light-transmitting regions 9a and fallen on the optically-coupled layer 12 is guided toward the light-shielding regions 9A adjacent to the light-transmitting regions 9a in the X direction.

A component of light that is transmitted by the second transparent layer 12b and falls on a lower layer falls on all of the second transparent layers 12b located on a lower layer side. This causes guided light 6c to be generated under the same condition as Eq. (1). Although rays of guided light are generated on all of the second transparent layers 12b, FIG. 2A represents only rays of guided light that are generated on two layers. The guided light 6c, which is generated on the lower layer side, also propagates in the X direction in the XY plane. The rays of guided light 6b and 6c propagate while radiating light upward and downward at an angle θ (in the example shown in FIG. 2A, θ=0°) with respect to the normal to the waveguide plane (XY plane). Those components of the rays of radiated light 6B1 and 6C1 which travel upward (toward the reflecting film) directly below the light-shielding regions 9A is reflected by the light-shielding regions 9A to turn into light 6B2 that travels downward along the normal to the plane of reflection (XY plane). The rays of light 6B1, 6C1, and 6B2 satisfy Eq. (1) with respect to the second transparent layers 12b. Therefore, portions of the rays of light 6B1, 6C1, and 6B2 turn back into the rays of guided light 6b and 6c. These rays of guided light 6b and 6c also generate new rays of radiated light 6B1 and 6C1. These processes are repeated. As a whole, directly below the light-transmitting regions 9a, a component that did not turn into guided light is transmitted by the optically-coupled layer 12 and falls on the microlenses 11a as transmitted light 6d. As a result, the component that did not turn into guided light is detected by the first pixels 10a. In actuality, a component that was finally radiated after being guided is added to the component that did not turn into guided light. However, such a component is treated herein as the component that did not turn into guided light. Directly below the light-shielding regions 9A, a component that turned into guided light is radiated and falls on the microlenses 11A as transmitted light 6D. As a result, the component that turned into guided light is detected by the second pixels 10A.

Light splits through the light-transmitting regions 9a onto the pixels located directly below the light-transmitting regions 9a and the pixels located on either side of those pixels (i.e. adjacent to those pixels in the X direction) and is detected by each of the pixels.

Let it be assumed that the amounts of light detected by the first pixels 10a facing the light-transmitting regions 9a1, 9a2, 9a3, and 9a4 shown in FIG. 2B are q1, q2, q3, and q4, respectively. Let it also be assumed that the amounts of light detected by the second pixels 10A facing the light-shielding regions 9A1, 9A2, 9A3, and 9A4 shown in FIG. 2B are Q1, Q2, Q3, and Q4, respectively. q1 to q4 represent the detected amounts of light that did not turn into guided light. Q1 to Q4 represent the detected amounts of light that turned into guided light. An amount of light that turned into guided light is not detected by the first pixel 10a located directly below the light-transmitting region 9a1. Meanwhile, an amount of light that did not turn into guided light is not detected by the second pixel 10A located directly below the light-shielding region 9A2.

Note here that, at a detecting position located directly below the light-transmitting region 9a1, the amount of light that turned into guided light Q0=(Q1+Q2)/2 (or Q0=(Q1+Q2+Q3+Q4)/4) is defined. Similarly, at a detecting position located directly below the light-shielding region 9A2, the amount of light that did not turn into guided light q0=(q1+q2)/2 (or q0=(q1+q2+q3+q4)/4) is defined. That is, in a region (a light-shielding region or a light-transmitting region), the average value of the amounts of light that are detected by pixels located directly below regions adjacent in the X direction and/or the Y direction with that region at the center is defined.

By applying these definitions to all regions, the detected amount of light that did not turn into guided light and the detected amount of light that turned into guided light can be defined for all of the pixels of the photodetector 10.

The arithmetic circuit 14 performs arithmetic processing such as the generation of an optical distribution image representing a distribution of degree of coherence using the detected amount of light that did not turn into guided light and the detected amount of light that turned into guided light as interpolated on the basis of such definitions as those described above. The arithmetic circuit 14 generates an optical distribution image by calculating the value of the ratio between these two detected amounts of light (or the value of the ratio of each amount of light with respect to the sum of these amounts of light) for each pixel and assigning the value to that pixel.

Figure 3:
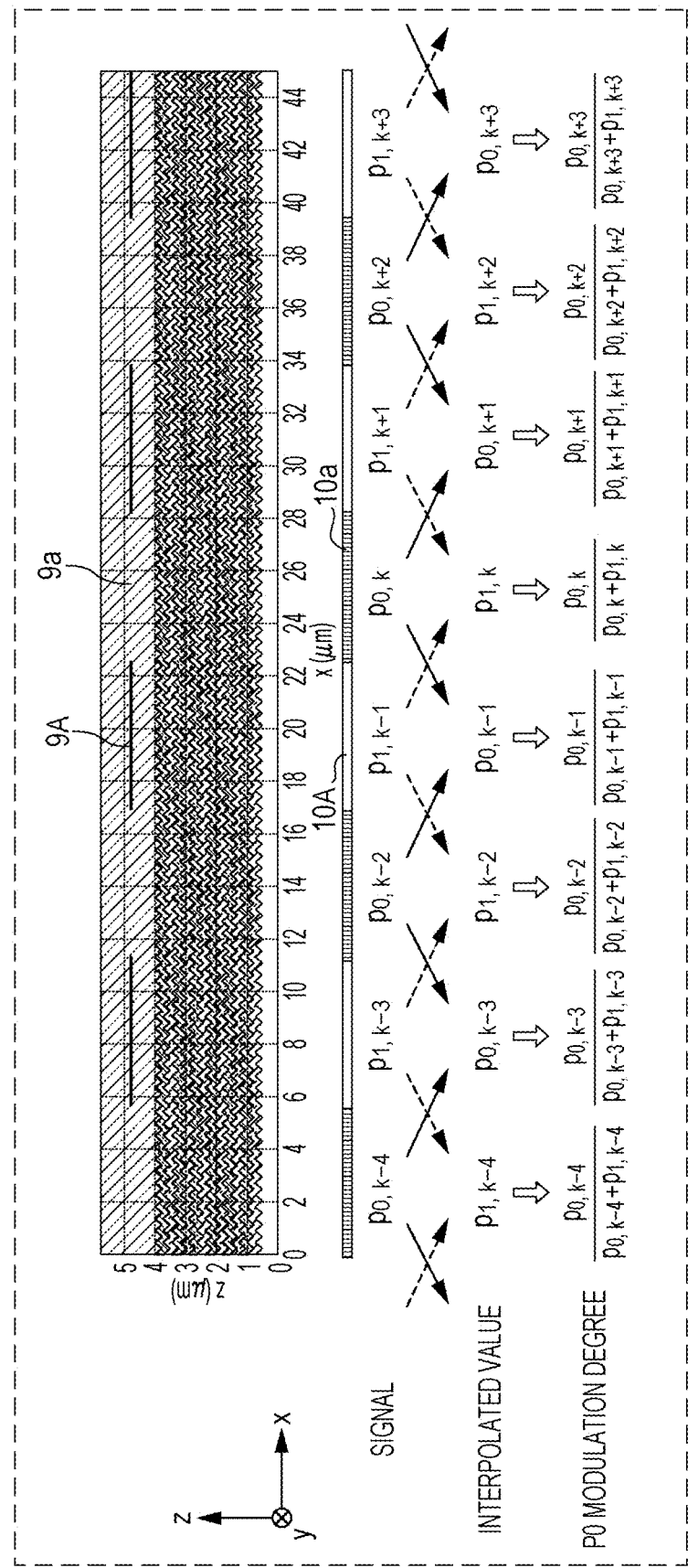
FIG. 3 shows a method of signal processing by the photo-detection apparatus.

FIG. 3 shows a method of signal processing by the photo-detection apparatus 13. In FIG. 3, eight pixels including first pixels 10a and second pixels 10A are arranged along the grating vector of each of the grating 12d. The first pixels 10a and the second pixels 10A face light-transmitting regions 9a and light-shielding regions 9A, respectively. Let it be assumed that $p_{0,k-4}$, $p_{1,k-3}$, $p_{0,k-2}$, $p_{1,k-1}$, $p_{0,k}$, $p_{1,k+1}$, $p_{0,k+2}$, and $p_{1,k+3}$ denote signals that are detected by the eight pixels. For example, the average value $(p_{1,k-1}+p_{1,k+1})/2$ of the signals $p_{1,k-1}$ and $p_{1,k+1}$ that are detected by pixels located on either side of the pixel that detects the signal $p_{0,k}$ is defined as an interpolated value $p_{1,k}$. Similarly, the average value $(p_{0,k-2}+p_{0,k})/2$ of the signals $p_{0,k-2}$ and $p_{0,k}$ that are detected by pixels located on either side of the pixel that detects the signal is defined as an interpolated value $p_{0,k-1}$. From the signal $p_{0,k}$ and the interpolated value $p_{1,k}$, a P0 modulation degree $p_{0,k}/(p_{0,k}+p_{1,k})$ or a P1 modulation degree $p_{1,k}/(p_{0,k}+p_{1,k})$ is calculated. In the example of discussion, these modulation degrees are utilized as detected signals. The P0 modulation degree is a modulation degree based on light having fallen on the first pixels 10a, and the P1 modulation degree is a modulation degree based on light having fallen on the second pixels 10A.

Figure 4A:
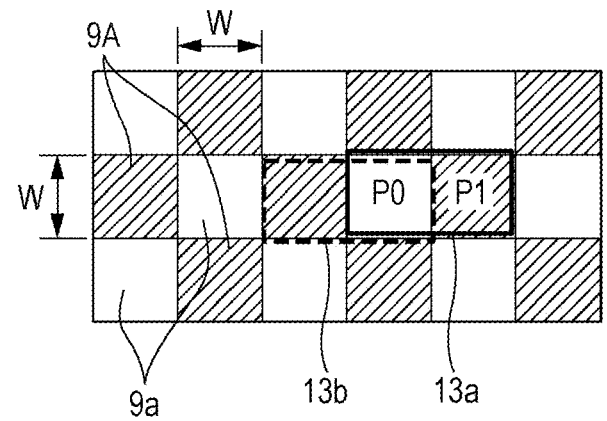
FIG. 4A is a plan view showing a pattern of light-transmitting regions and light-shielding regions.
Figure 4B:
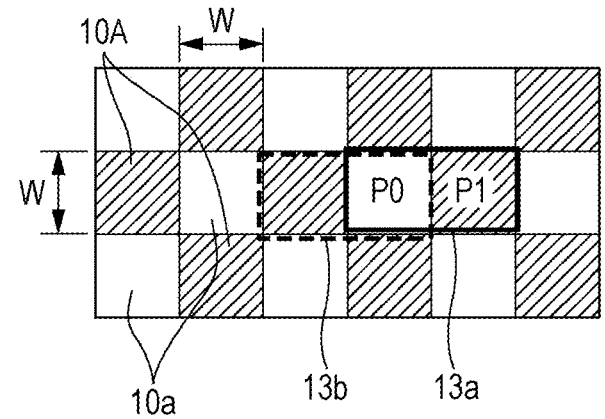
FIG. 4B is a plan view showing a pattern of detectors.
Figure 4C:
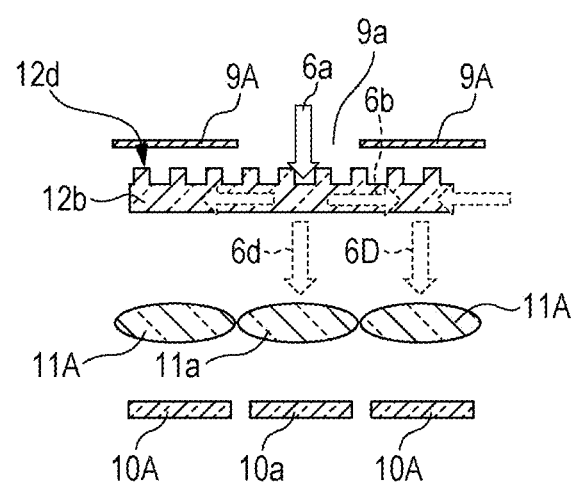
FIG. 4C is a cross-sectional view showing a positional relationship between light-transmitting regions, light-shielding regions, and detectors.

FIG. 4A is a plan view showing a pattern of light-transmitting regions 9a and light-shielding regions 9A. FIG. 4B is a plan view showing a pattern of first pixels 10a and second pixels 10A. FIG. 4C is a cross-sectional view showing a positional relationship between light-transmitting regions 9a, light-shielding regions 9A, first pixels 10a, and second pixels 10A. The first pixels 10a and the second pixels 10A are located directly below the light-transmitting regions 9a and the light-shielding regions 9A, respectively. In general, assuming P0 is a detecting region located directly below a light-transmitting region 9a and P1 is a detecting region located directly below a light-shielding region 9A, P0 and P1 form a checkered pattern with a size of W×W. A solid-line pixel region 13a includes one P0 and one P1. A dashed-line pixel region 13b includes one P0 and one P1, too. Any displacement of a pixel region by a light-shielding width (=W) in the XY plane results in inclusion of one P0 and one P1, albeit with a change in positional relationship. As mentioned above, the detected amounts of light is subjected to interpolation processing according to the equations of q0 and Q0. Assuming that resolution is determined by pixel size, the resolution is 2 W×W, which is the size of the pixel regions 13a and 13b. However, the same interpolation processing holds no matter in which direction the pixels are moved by the width W in the XY plane. Therefore, the resolution finished with interpolation processing improves to W×W.

The following describes the appearance of incident light of one pulse oscillation passing through the optically-coupled layer 12 and being received by the photodetector 10.

Figure 5A:
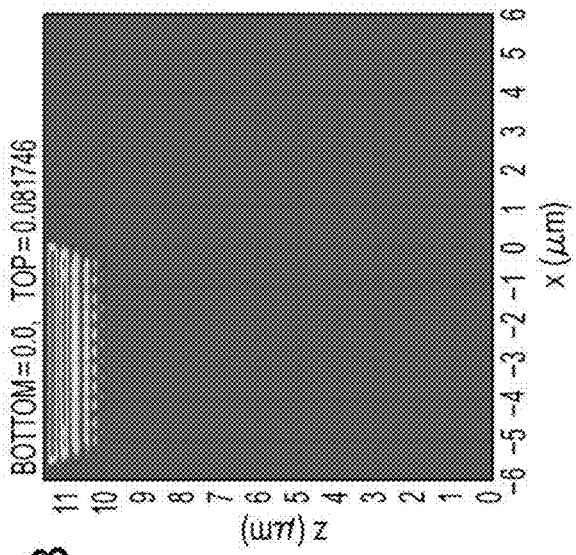
FIG. 5A is a cross-sectional view taken along the same plane as FIG. 2A.

FIG. 5A is a cross-sectional view taken along the same plane as FIG. 2A. FIGS. 5B to 5H are diagrams showing results, ordered in time elapsed, of an electromagnetic analysis of a light intensity distribution by an FDTD (finite-difference time-domain) method as drawn in correspondence with FIG. 5A. The width W of each of the light-transmitting regions 9a and the light-shielding regions 9A in the X direction was 5.6 μm. Each of the pitches between the gratings 12d was 0.46 μm. The depth of each of the gratings 12d in the Z direction was 0.2 μm. Each of the second transparent layers 12b was a $Ta_2O_5$ film. The thickness $t_1$ of each of the second transparent layers 12b in the Z direction was 0.34 μm. Each of the first transparent layers 12c was a $SiO_2$ film. The thickness $t_2$ of each of the first transparent layers 12c in the Z direction was 0.22 μm.

Figure 5B:
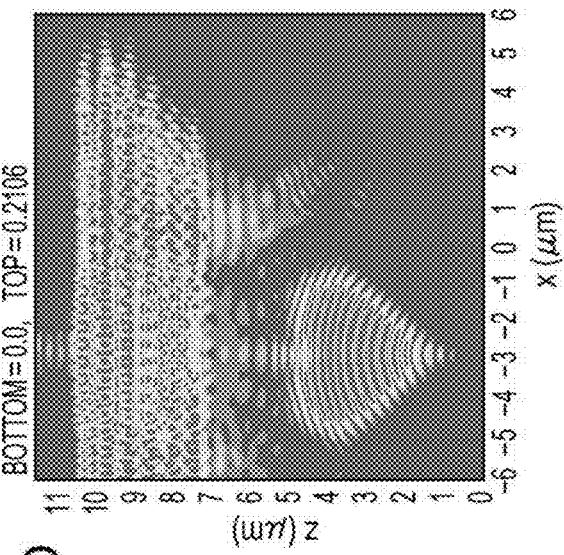
FIG. 5B shows a result of an electromagnetic analysis of a light intensity distribution by an FDTD method as drawn in correspondence with FIG. 5A.
Figure 5C:
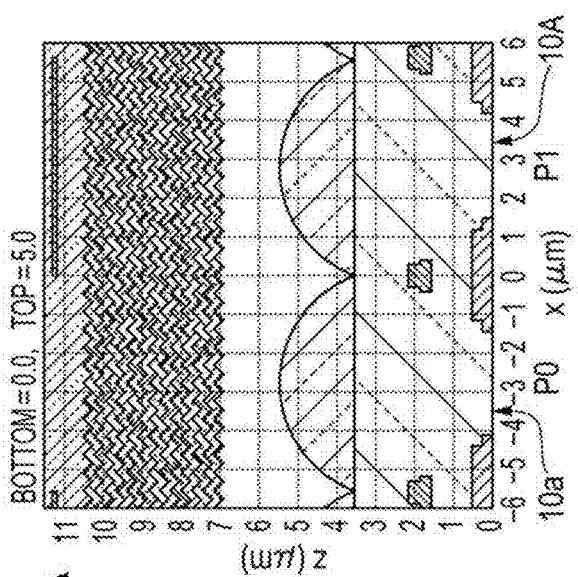
FIG. 5C shows a result of the electromagnetic analysis of the light intensity distribution by the FDTD method as drawn in correspondence with FIG. 5A.
Figure 5D:
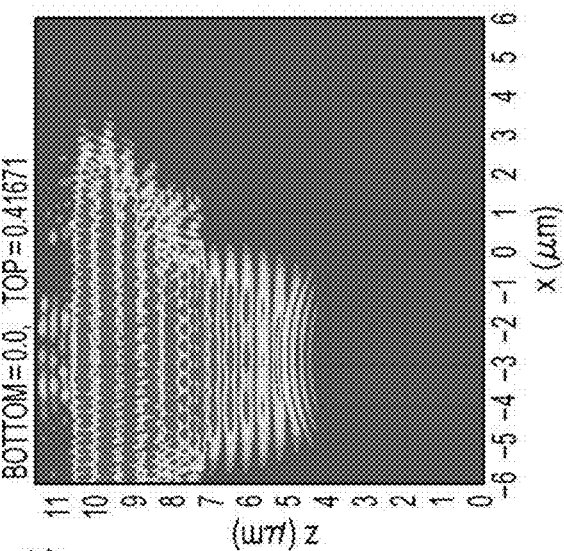
FIG. 5D shows a result of the electromagnetic analysis of the light intensity distribution by the FDTD method as drawn in correspondence with FIG. 5A.
Figure 5F:
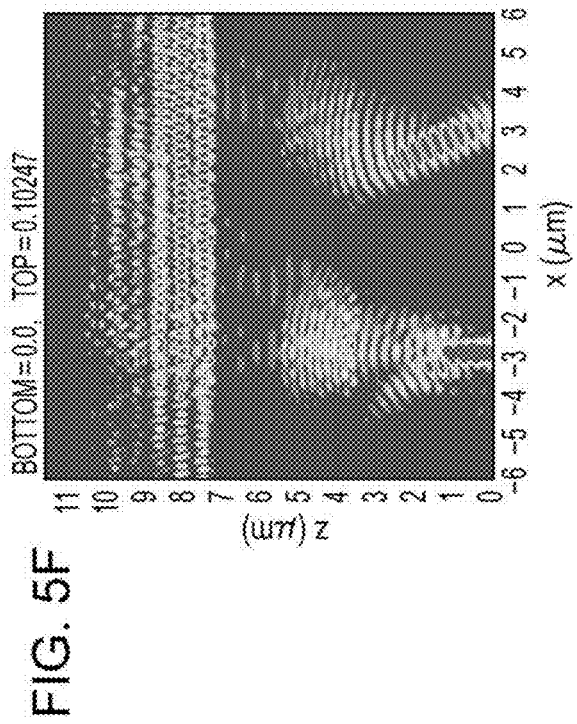
FIG. 5F shows a result of the electromagnetic analysis of the light intensity distribution by the FDTD method as drawn in correspondence with FIG. 5A.
Figure 5H:
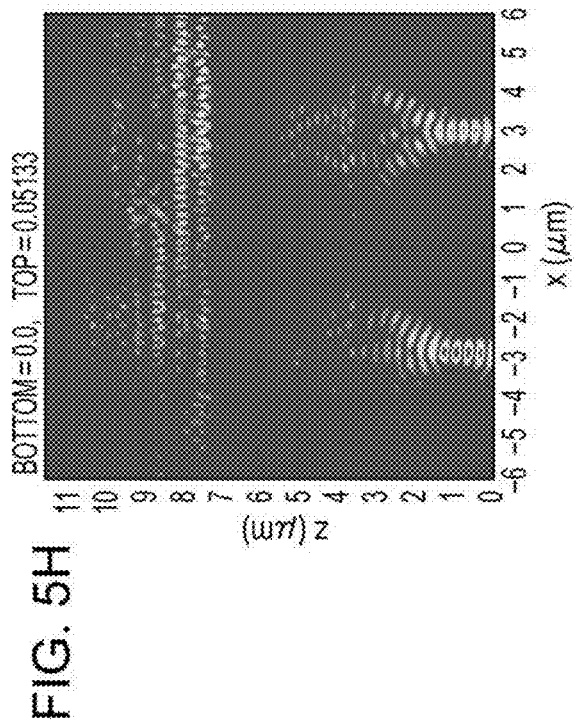
FIG. 5H shows a result of the electromagnetic analysis of the light intensity distribution by the FDTD method as drawn in correspondence with FIG. 5A.
Figure 5E:
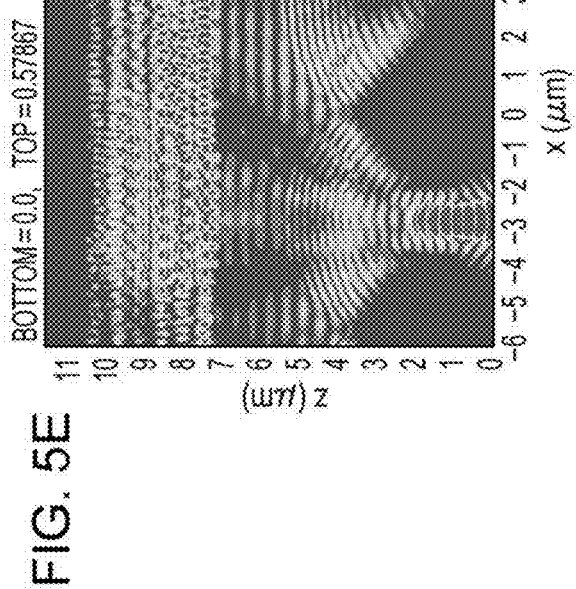
FIG. 5E shows a result of the electromagnetic analysis of the light intensity distribution by the FDTD method as drawn in correspondence with FIG. 5A.
Figure 5G:
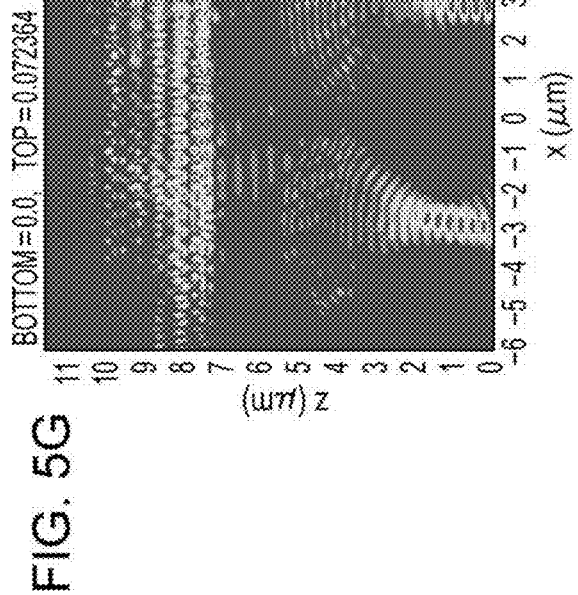
FIG. 5G shows a result of the electromagnetic analysis of the light intensity distribution by the FDTD method as drawn in correspondence with FIG. 5A.

In FIG. 5B, S-polarized light 6a with a wavelength $\lambda_0$ of 850 nm pulse-oscillated at a half-value width of 11 fs (3.3 μm in propagation distance terms) is transmitted by the light-transmitting region 9a. In FIG. 5C, while the oscillation of the light 6a ends, rays of guided light 6b and 6c that propagate through the second transparent layer 12b stacked are generated, and a component that did not turn into guided light is directly transmitted by the optically-coupled layer 12 and falls on the microlens 11a as light 6d. In FIG. 5D, the rays of guided light 6b and 6c propagate to a lower position than the light-shielding region 9A while radiating rays of light 6B1 and 6C1 upward and downward. Meanwhile, the transmitted light 6d is condensed by the microlens 11a to a higher position than the first pixel 10a. In FIG. 5E, the transmitted light 6d falls on the first pixel 10a. Meanwhile, the rays of radiated light 6B1 and 6C1 and reflected light 6B2 form radiated light 6D that falls on and is condensed by the microlens 11A. In FIGS. 5F to 5H, the transmitted light 6d and the radiated light 6D fall on the first pixel 10a and the second pixel 10A, respectively, while being condensed.

It should be noted that, as can be seen from FIGS. 5E to 5H, the rays of guided light 6b and 6c are not completely radiated within a range below the light-shielding region 9A. As a result, portions of the rays of guided light 6b and 6c reach the adjacent light-transmitting region 9a on the right side. A radiation loss coefficient (i.e. the ease with which guided light is radiated) is made higher by increasing the depth of each of the gratings 12d. Therefore, increasing the depth of each of the gratings 12d in a region below the light-shielding region 9A increases the amount of radiated light, thus making it possible to increase the amount of detected light.

FIG. 6A is a cross-sectional view showing a positional relationship between incident light on four light-transmitting regions 9a in the example of discussion and three pixels located therebelow. Rays of light differing randomly in phase from one another fall on the four light-transmitting regions 9a. In FIG. 6A, ω represents the angular frequency of light ($\omega=2\pi c/\lambda_0$, where c is the speed of light), t represents time, r1, r2, r3, and r4 represent random functions (functions that take random values of 0 to 1), and a represents a random coefficient (amplitude of a random value).

Figure 6B:
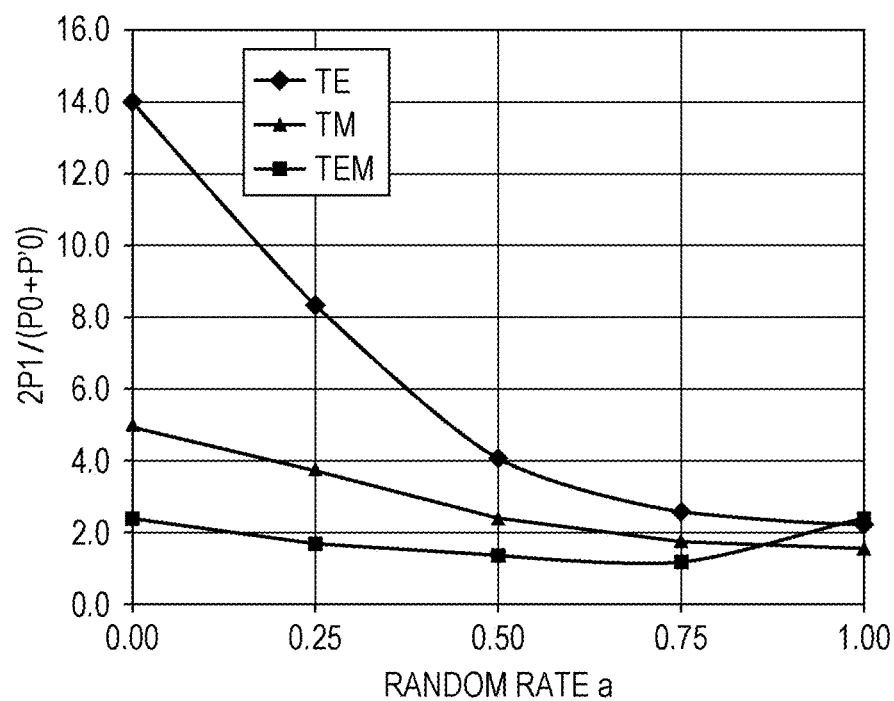
FIG. 6B shows an analysis result showing a relationship between the phase random coefficient a of incident light and a detected signal.

FIG. 6B shows an analysis result showing a relationship between the phase random coefficient a of incident light and a detected signal. Let it be assumed that a pixel located directly below a light-shielding regions 9A located in the middle of the four light-transmitting regions 9a is a second pixel 10A and pixels located directly below light-transmitting regions 9a adjacent to the light-shielding region 9A on both sides are first pixels 10a and 10a'. Let it also be assumed that the amounts of light detected by the second pixel 10A, the first pixel 10a, and the first pixel 10a' are P1, P0', and P0'', respectively, and the detected signal is defined by 2P1/(P0+P0'). In FIG. 6B, the rhombic mark indicates the result of an analysis conducted under the condition of TE mode incidence (S polarization), the square mark indicate the result of an analysis conducted under the condition of TM mode incidence (P polarization), and the triangular mark indicates the result of an analysis conducted under the condition of TEM mode incidence (random polarization, circular polarization, or 45-degree polarization). With attention focused on the conditions of TE mode incidence and TEM mode incidence, the detected signal lowers as the coefficient a increases. a=0 is equivalent to a coherent case of uniform phase. a=1 is equivalent to an incoherent state. Therefore, the degree of coherence (phase randomness) of the incident light can be found from the magnitude of the detected signal. Similarly, a difference in phase of the incident light can be measured from the magnitude of the detected signal.

The following shows the results of calculation made by a ray-tracing method based on a Monte Carlo method, assuming that the subject is a human head.

Figure 7A:
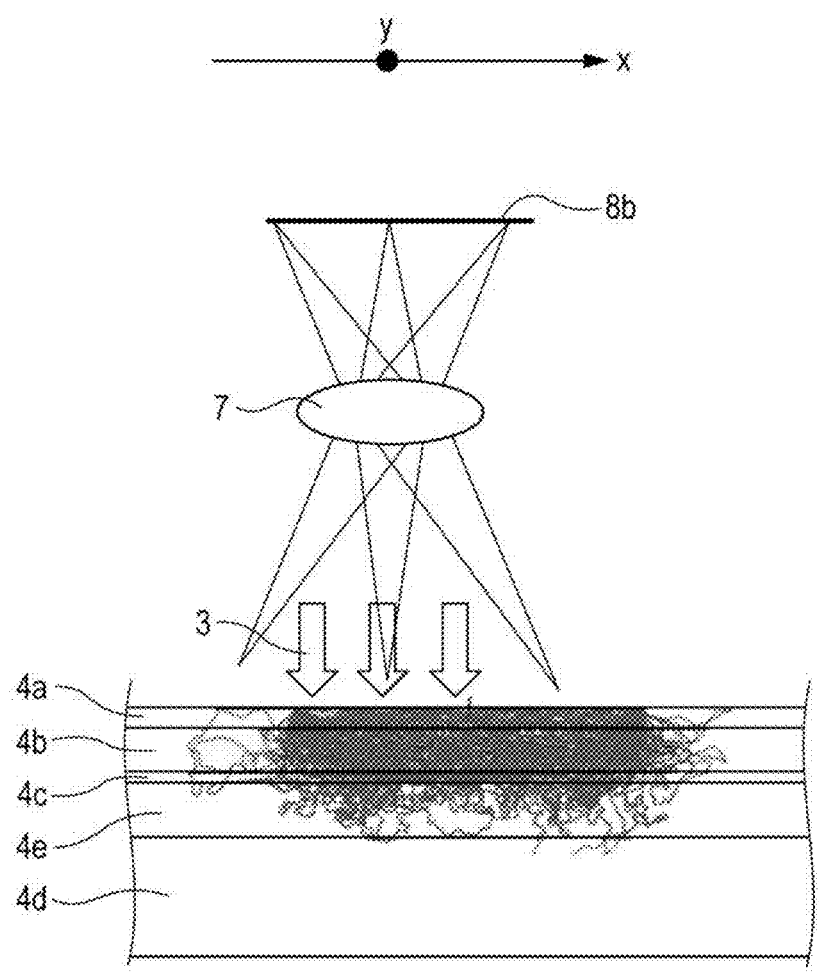
FIG. 7A shows the whole optical arrangement and the appearance of ray tracing.
Figure 7B:
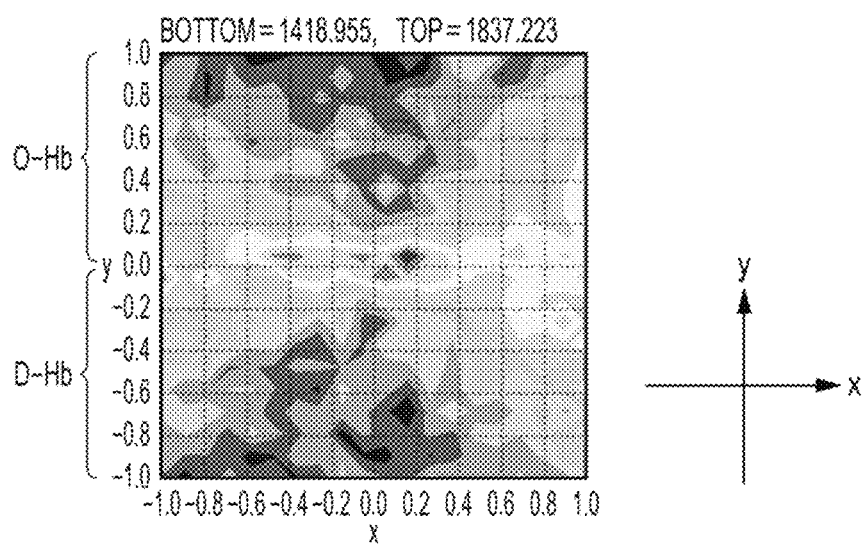
FIG. 7B shows a light intensity distribution.
Figure 7C:
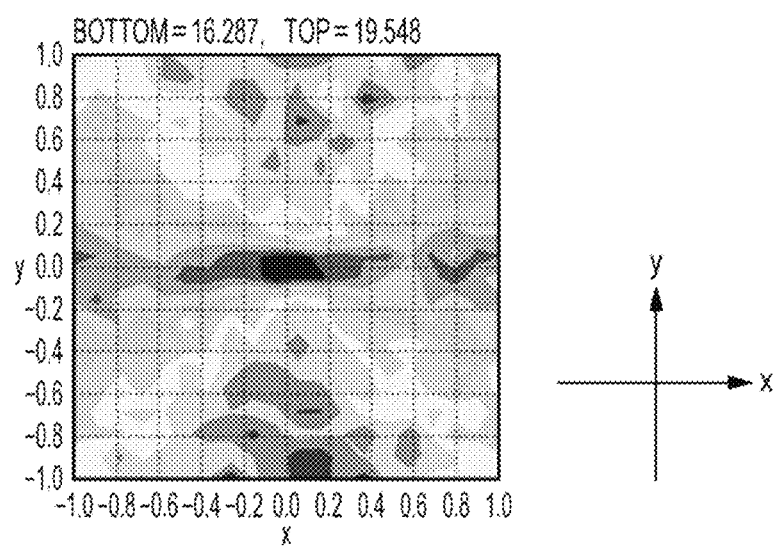
FIG. 7C shows an average distribution of optical path length.
Figure 7D:
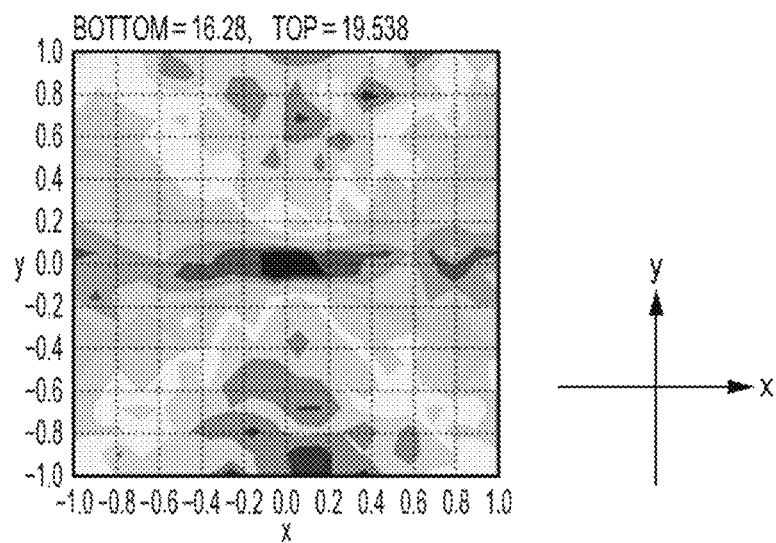
FIG. 7D shows a standard deviation distribution of optical path length.

FIG. 7A shows the whole optical arrangement and the appearance of ray tracing in the present analysis. FIGS. 7B to 7D show the results of an analysis in which an image 8b at a detecting position was divided into 20×20 regions. FIG. 7B shows a light intensity distribution. FIG. 7C shows an average distribution of optical path length. FIG. 7D shows a standard deviation distribution of optical path length. As shown in FIG. 7A, the human head includes a scalp 4a, a cranium 4b, a cerebrospinal fluid (CSF) layer 4c, a blood layer 4e, and a gray matter 4d. Table shows the respective absorption coefficients (1/mm), scattering coefficients (1/mm), anisotropic scattering parameters, and film thicknesses (mm) of the scalp 4a, the cranium 4b, the cerebrospinal fluid (CSF) 4c, the blood layer 4e, and the gray matter 4d. The blood layer 4e is an arrangement of an oxyhemoglobin layer and a deoxyhemoglobin layer that are laid side by side in the direction of the normal to the plane at the surface of paper.

TABLE

| | Absorption coefficient (1/mm) | Scattering coefficient (1/mm) | Anisotropic scattering parameter | Film thickness (mm) |
|---|---|---|---|---|
| Scalp | 0.030 | 0.73 | 0.90 | 2.0 |
| Cranium | 0.012 | 1.80 | 0.90 | 4.0 |
| CSF layer | 0.002 | 0.30 | 0.90 | 1.0 |
| Blood layer (oxyhemoglobin layer/deoxyhemoglobin layer) | 0.28/0.16 | 50.5/66.8 | 0.992 | 5.0 |
| Gray matter | 0.036 | 2.30 | 0.90 | 10.0 |

The analytical region measures 60 mm×60 mm in the X and Y directions and 22 mm in the Z direction. Rays of light propagating beyond this region were excluded from the calculations. It was assumed that light 3 falling on the human head was light falling perpendicularly on nine places arranged in a three-by-three matrix at intervals of 5 mm in the X and Y directions and centered at a position displaced by 15 mm in a −X direction from the center (X=Y=0) of the surface of the scalp 4a. A condensing lens was placed as the lens optical system 7 in a position 1000 mm away from the surface of the scalp 4a. The image 8b in the image surface position was calculated from the rays of light captured, assuming that the numerical aperture (sin α) on the object side is NA=0.1. The detecting regions of scattering light shown in FIGS. 7B to 7D fall within a width range of 0.8 mm in the X and Y directions centered at a position displaced by 15 mm in a +X direction from the center (X=Y=0) of the surface of the scalp 4a. In FIG. 7B, a whiter region has a higher intensity. In FIGS. 7C and 7D, a whiter region has a larger value. A region where Y>0 is equivalent to the oxyhemoglobin layer, and a region where Y<0 is equivalent to the deoxyhemoglobin layer. In any of FIGS. 7B to 7D, there is a slight difference between the oxyhemoglobin layer and the deoxyhemoglobin layer. Since the image is inverted by the condensing lens, the positions of the oxyhemoglobin layer and the deoxyhemoglobin layer are a reversal of their actual positions.

Let it be assumed that the light source 2 generates light with a coherence length $\sigma_0$. When the standard deviation of optical path lengths is less than or equal to the coherence length $\sigma_0$ rays of light that are received are highly likely to be in the same wave packet and have a high phase correlation with each other. At this point in time, the rays of light that are received appear as a welter of bright places and dark places. Meanwhile, when the standard deviation of optical path lengths is greater than or equal to $\sigma_0$ the rays of light that are received are highly likely to be in different wave packets and lose their phase correlation with each other (see FIG. 17). At this point in time, the rays of light that are received become uniform in brightness regardless of location. As described with reference to FIG. 6B, the degree of coherence of the incident light relates to the detected signal 2P1/(P0+P0'). Therefore, whether a standard deviation of the incident light is greater than or equal to the coherence length $\sigma_0$ can be determined on the basis of the magnitude of the detected signal.

Figure 7E:
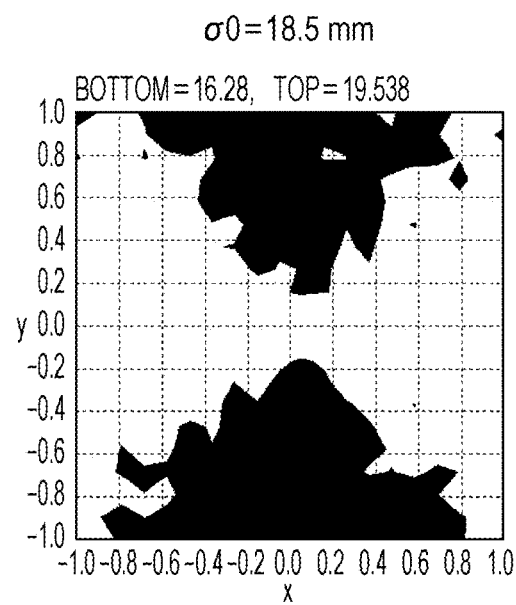
FIG. 7E shows a distribution of detected signals in a case where σ=18.5 mm.
Figure 7F:
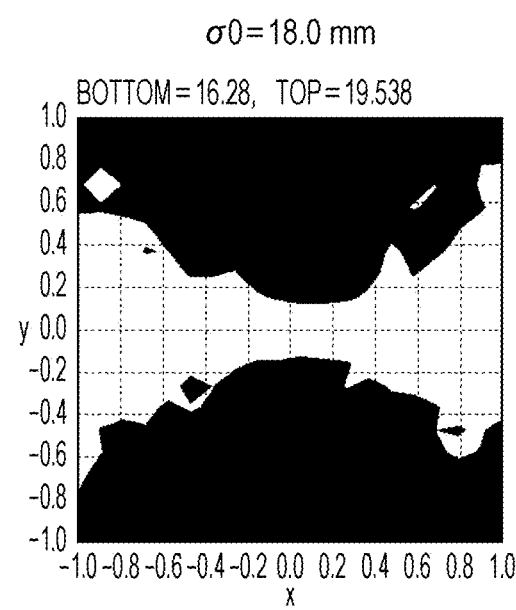
FIG. 7F shows a distribution of detected signals in a case where $\sigma_0$=18.0 mm.

FIG. 7E shows a distribution of detected signals in a case where $\sigma_0$=18.5 mm. FIG. 7F shows a distribution of detected signals in a case where $\sigma_0$=18.0 mm. The black regions in the drawings represent regions where the detected signals are uniformly small. In the example of $\sigma_0$=18.5 mm shown in FIG. 7E, the detected signals are small in regions where the standard deviation of optical path lengths exceeds 18.5 mm (black regions in FIG. 7E). Meanwhile, in the example of $\sigma_0$=18.0 mm shown in FIG. 7F, the detected signals are small in wider regions than in the example shown in FIG. 7E. In FIGS. 7E and 7F, the detected signals vary randomly in magnitude according to location in regions other than the black regions. The appearance of scattering within the subject can be found by analyzing the black regions with the coherence length $\sigma_0$ as a parameter.

A high-frequency superposed semiconductor laser or a sweep light source that periodically sweeps the wavelength of a laser within the range of several nanometers to several tens of nanometers is at such a level as to be practically used as a light source that renders the coherence length variable. For example, a semiconductor laser that is driven by a high-frequency superposed circuit (generally at a frequency of 300 MHz) oscillates at a coherence length within the range of 0.1 mm to 0.2 mm. Then, the coherence length can be varied within the range of 0.2 mm to several tens of millimeters by varying the frequency or amplitude (e.g. lowering the frequency) of the superposed circuit. The variable range can be changed by combining the high-frequency superposed circuit with a DFB laser or the like. In the sweep light source, the coherence length can be varied within the range of 0.3 mm to several tens of millimeters by varying the range of fluctuations in wavelengths or the cycle frequency. Note, however, that in a case where the sweep light source is used, the bandpass filter 9p is used in some cases to limit the wavelength of light that falls on the optically-coupled layer 12. Alternatively, a desired coherence length can be obtained by combining a light source with a wide line width, such as an LED, and a narrowband bandpass filter. Two or more light sources with different wavelengths may be used as the light source. When rays of light from these light sources scatter through the subject and fall on the light-transmitting regions 9a, a beat is generated according to the principles explained in FIG. 18E. As a result, the coherence length becomes shorter according to the wavelength difference between the rays of light that are emitted from the two light sources. Note, however, that, in this case, too, the bandpass filter 9p is used in some cases to limit the wavelength of light that falls on the optically-coupled layer 12. In a case where light sources with different wavelengths are used, an operation of changing the ratio of emission intensity between the light sources may be performed in an interlocked fashion.

By thus using the photo-detection system 100 according to the example of discussion, a distribution difference between the oxyhemoglobin layer and the deoxyhemoglobin layer, which are located behind the cranium 4b of the subject shown in FIG. 7A, can be detected as an output difference between electrical signals. This method makes it possible to significantly simplify measurements, as it does not require time division unlike the method (second conventional example) shown in FIGS. 19A and 19B for detecting a light intensity distribution image. Further, the resolution of measurements can be enhanced, as the appearance of scattering within the subject can be compared and analyzed simply by changing the coherence length of the light source.

In the photo-detection apparatus according to the example of discussion, as shown in FIGS. 5E to 5H, portions of the rays of guided light 6b and 6c reach the adjacent light-transmitting region 9a. Therefore, there occurs crosstalk in which the P0 modulation degree $p_{0,k}/(p_{0,k}+p_{1,k})$ and the P1 modulation degree $p_{1,k}/(p_{0,k}+p_{1,k})$ are mixed with radiated light from guided light having propagated from a position that is distant from the pixels. Due to the influence of this crosstalk, there has been a possibility that the photo-detection apparatus according to the example of discussion may deteriorate in resolution of a detected signal.

To address this problem, the inventor conceived of a novel imaging apparatus that can precisely measure a degree of phase difference or coherence as an optical distribution image.

A photo-detection system according to an aspect of the present disclosure includes:
a photo-detection apparatus; and
an arithmetic circuit.

The photo-detection apparatus includes
a light-shielding film including light-transmitting regions and light-shielding regions, the light-transmitting regions and the light-shielding regions being alternately arranged in at least a first direction within a plane,
an optically-coupled layer facing the light-shielding film, the optically-coupled layer including a grating which generates a propagating light that propagates in the first direction and a transmitting light that transmits the optically-coupled layer when incident light of a predetermined wavelength enters the light-transmitting region, and
a photodetector having an imaging area, the photodetector including first photo-detection cells and second photo-detection cells, the first photo-detection cells and the second photo-detection cells being arranged on the imaging area, each of the first photo-detection cells corresponding to at least one of the light-transmitting regions, each of the second photo-detection cells corresponding to at least one of the light-shielding regions.

The arithmetic circuit corrects each of first signals that are obtained from at least part of the first photo-detection cells by using two of the first signals that are obtained from two of the first photo-detection cells located closest in the first direction and a direction opposite to the first direction to each of the at least part of the first photo-detection cells.

The arithmetic circuit corrects each of second signals that are obtained from at least part of the second photo-detection cells by using two of the second signals that are obtained from two of the second photo-detection cells located closest in the first direction and the direction opposite to the first direction to each of the at least part of the second photo-detection cells.

The arithmetic circuit outputs, based on the first signals thus corrected and the second signals thus corrected, third signals each representing coherence of light having entered a position of each of the first and second photo-detection cells.

This configuration makes it possible to measure the degree of coherence or phase of light by calculating detected signals such as P0 modulation degrees or P1 modulation degrees using these corrected values.

A photo-detection system according to another aspect of the present disclosure includes:
a photo-detection apparatus; and
an arithmetic circuit.

The photo-detection apparatus includes
a light-shielding film in which light-transmitting regions and light-shielding regions, the light-transmitting regions and the light-shielding regions being alternately arranged in at least a first direction within a plane,
an optically-coupled layer facing the light-shielding film, the optically-coupled layer including a grating which generates a propagating light that propagates in the first direction and a transmitting light that transmits the optically-coupled layer when incident light of a predetermined wavelength enters the light-transmitting regions, and
a photodetector having an imaging area, the photodetector including first photo-detection cells and second photo-detection cells, the first photo-detection cells and the second photo-detection cells being arranged on the imaging area, each of the first photo-detection cells corresponding to at least one of the light-transmitting regions, each of the second photo-detection cells corresponding to at least one of the light-shielding regions.

The arithmetic circuit generates, based on first signals that are obtained from the first photo-detection cells and second signals that are obtained from the second photo-detection cells, third signals each representing coherence of light having entered a position of each of the first and second photo-detection cells.

The arithmetic circuit generates at least one selected from the group consisting of an average value of the third signals, a standard deviation of the third signals, a ratio between the standard deviation and the average value, and a ratio between an average value of a first portion of the third signals and an average value of a second portion of the third signals in positions of at least a part of the first photo-detection cells and the second photo-detection cells that are included in a region of the imaging plane.

The first portion of the third signals is based on light having entered the positions of the first photo-detection cells, and the second portion of the third signals is based on light having entered the positions of the second photo-detection cells.

This configuration makes it possible to measure variations in the degree of coherence or phase of light within an area.

A light-emitting apparatus according to still another aspect of the present disclosure includes:
a first light source that emits a first coherent light having a first wavelength;
a second light source that emits a second coherent light having a second wavelength that, with changes in temperature of the second light source, varies within a wavelength range including the first wavelength; and
an optical multiplexer that multiplexes the first coherent light and the second coherent light.

With this configuration, the variability of the coherence length, which is needed for measurements, can be more easily achieved by controlling the temperature of a light source.

The following describes more specific embodiments of the present disclosure. It should be noted that each of the embodiments described below shows a general or specific example. In the embodiments described below, the numerical values, the shapes, the materials, the constituent elements, and the placement of the constituent elements are mere examples and not intended to limit the present disclosure. Those of the constituent elements in the embodiments described below which are not recited in an independent claim representing the most generic concept are described as optional constituent elements.

First Embodiment

The present embodiment is all the same in configuration as the example of discussion except for the method for performing an arithmetic operation on a detected signal. Therefore, common elements are given the same reference numerals and not described in detail below.

Figure 8:
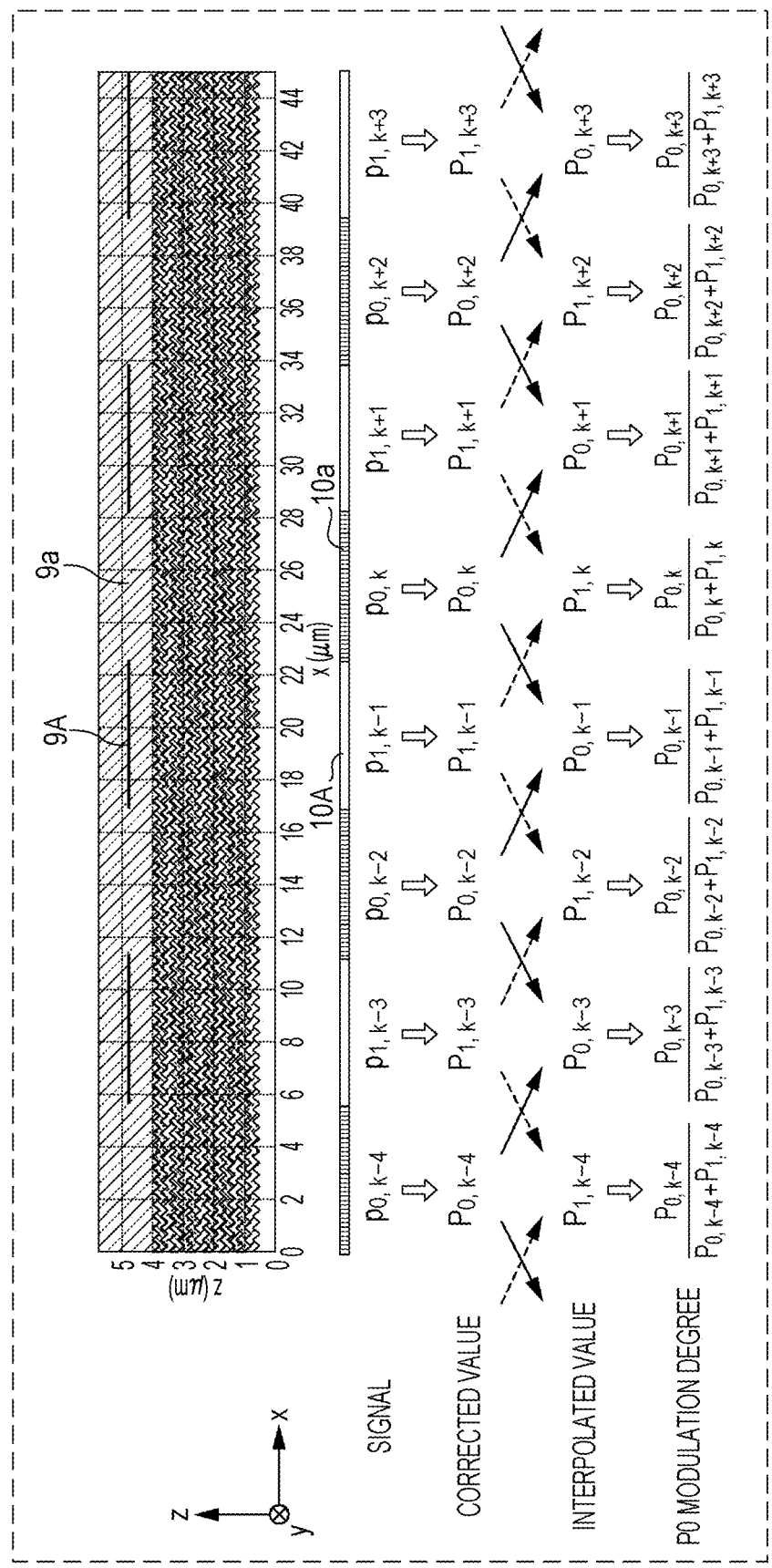
FIG. 8 shows a method for signal processing by a photo-detection apparatus according to a first embodiment.
Figure 9:
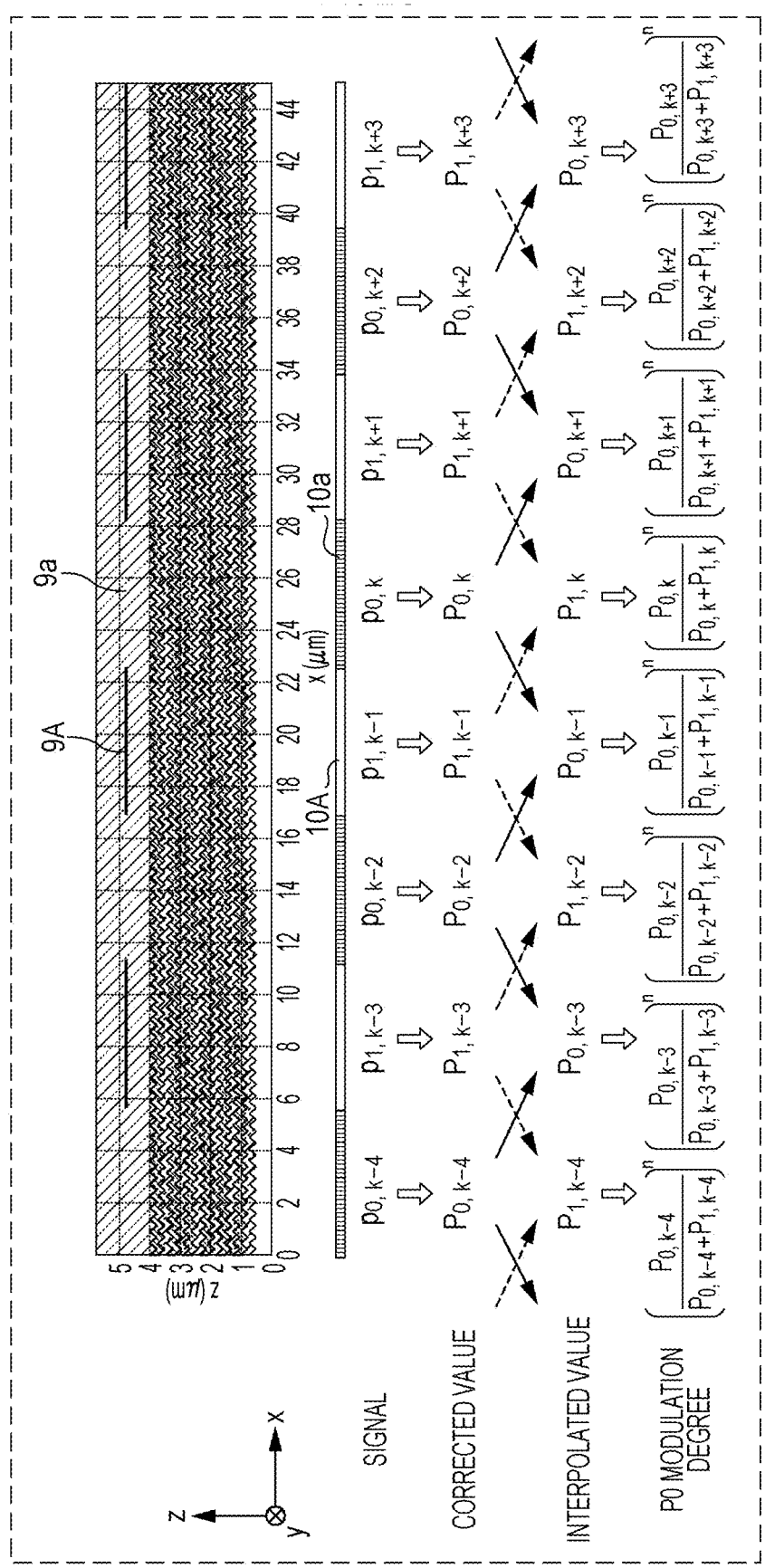
FIG. 9 shows another method for signal processing by the photo-detection apparatus according to the first embodiment.

FIG. 8 shows a method for signal processing by a photodetection apparatus according to a first embodiment. FIG. 9 shows another method for signal processing by the photodetection apparatus according to the first embodiment. In FIGS. 8 and 9, eight pixels including first pixels 10a and second pixels 10A are arranged along the grating vector of each of the grating 12d. The second pixels 10A and the first pixels 10a face light-shielding regions 9A and light-transmitting regions 9a, respectively.

First, the corrected values $P_{0,k-4}$, $P_{1,k-3}$, $P_{0,k-2}$, $P_{1,k-1}$, $P_{0,k}$, $P_{1,k+1}$, $P_{,k+2}$, and $P_{,k+3}$ are calculated from the signals $p_{0,k-4}$, $p_{1,k-3}$, $p_{0,k-2}$, $p_{1,k-1}$, $p_{0,k}$, $p_{1,k+1}$, $p_{0,k+2}$, and $p_{1,k+3}$, which are detected by the eight pixels, according to the following crosstalk correction formulas Eq. (2) and Eq. (3):

$$P_{0,k} = \frac{1}{1+2a_0+2b_0}p_{0,k} + \frac{a_0}{1+2a_0+2b_0}(p_{0,k-2}+p_{0,k+2}) + \frac{b_0}{1+2a_0+2b_0}(p_{0,k-4}+p_{0,k+4}) \quad \text{Eq. (2)}$$

$$P_{1,k-1} = \frac{1}{1+2a_1+2b_1}p_{1,k-1} + \frac{a_1}{1+2a_1+2b_1}(p_{1,k-3}+p_{1,k+1}) + \frac{b_1}{1+2a_1+2b_1}(p_{1,k-5}+p_{1,k+3}) \quad \text{Eq. (3)}$$

The average value $(P_{1,k-1}+P_{1,k+1})/2$ of the corrected values $P_{1,k-1}$ and $P_{1,k+1}$ that correspond to pixels located on either side of the pixel that correspond to the corrected value $P_{0,k}$ is defined as an interpolated value $P_{1,k}$. Similarly, the average value $(P_{0,k-2}+P_{0,k})/2$ of the corrected values $P_{0,k-2}$ and $P_{0,k}$ that correspond to pixels located on either side of the pixel that corresponds to the corrected value $P_{1,k-1}$ is defined as an interpolated value $P_{0,k-1}$. From the corrected value $P_{0,k}$ and the interpolated value $P_{1,k}$, a P0 modulation degree $P_{0,k}/(P_{0,k}+P_{1,k})$ and a P1 modulation degree $P_{1,k}/(P_{0,k}+P_{1,k})$ is calculated. In the first embodiment, these modulation degrees are utilized as detected signals.

In the correction formulas of FIG. 8, the signal $p_{0,k}$, which is detected by a pixel corresponding to a light-transmitting region 9a, is corrected by using the signals $p_{0,k-4}$, $p_{0,k-2}$, $p_{0,k+2}$, and $p_{0,k+4}$, which are detected by pixels that are closest and second closest in the +X and −X directions to the pixel that detects the signal $p_{0,k}$, and two correction coefficients $a_0$ and $b_0$. The sum of the signals $p_{0,k-4}$, $p_{0,k-2}$, $p_{0,k}$, and $p_{0,k+2}$ and a coefficient of the signal $p_{0,k+4}$ is normalized to be 1. Similarly, the signal $p_{1,k-1}$, which is detected by a pixel corresponding to a light-shielding region 9A, is corrected by using the signals $p_{1,k-5}$, $p_{1,k-3}$, $p_{1,k+1}$, and $p_{1,k+3}$, which are detected by pixels that are close to the pixel that detects the signal $p_{1,k-1}$, and two correction coefficients $a_1$ and $b_1$. The sum of the signals $p_{1,k-5}$, $p_{1,k-3}$, $p_{1,k-1}$, and $p_{1,k+1}$ and a coefficient of the signal $p_{1,k+3}$ is normalized to be 1. The method for calculating a modulation degree is the same as that of the example of discussion. In the first embodiment, the P0 modulation degrees and the P1 modulation degrees, which are calculated using the corrected values, are used as detected signals.

Next, another method for signal processing by the photodetection apparatus according to the first embodiment, which is shown in FIG. 9, is described. In the method shown in FIG. 9, the corrected values $P_{0,k-4}$, $P_{1,k-3}$, $P_{0,k-2}$, $P_{1,k-1}$, $P_{0,k}$, $P_{1,k+1}$, $P_{,k+2}$, and $P_{,k+3}$ are calculated from the signals $p_{0,k-4}$, $p_{1,k-3}$, $p_{0,k-2}$, $p_{1,k-1}$, $p_{0,k}$, $p_{1,k+1}$, $p_{0,k+2}$, and $p_{1,k+3}$, which are detected by the eight pixels, according to the following crosstalk correction formulas Eq. (4) and Eq. (5):

$$P_{0,k} = \frac{1}{1+2a_0}p_{0,k} + \frac{a_0}{1+2a_0}(p_{0,k-2}+p_{0,k+2}) \quad \text{Eq. (4)}$$

$$P_{1,k-1} = \frac{1}{1+2a_1}p_{1,k-1} + \frac{a_1}{1+2a_1}(p_{1,k-3}+p_{1,k+1}) \quad \text{Eq. (5)}$$

In the correction formulas of FIG. 9, the signal $p_{0,k}$, which is detected by a pixel corresponding to a light-transmitting region 9a, is corrected by using the signals $p_{0,k-2}$ and $p_{0,k+2}$, which are detected by pixels that are closest in the +X and −X directions to the pixel that detects the signal $p_{0,k}$, and the correction coefficient $a_0$. The sum of the signals $p_{0,k-2}$ and $p_{0,k}$ and a coefficient of the signal $p_{0,k+2}$ is normalized to be 1. Similarly, the signal which is detected by a pixel corresponding to a light-shielding region 9A, is corrected by using the signals $p_{1,k-3}$ and $p_{1,k+1}$, which are detected by pixels that are close to the pixel that detects the signal $p_{1,k-1}$, and the correction coefficient $a_1$. The sum of the signals $p_{1,k-3}$ and $p_{1,k-1}$ and a coefficient of the signal $p_{1,k+1}$ is normalized to be 1. The method for calculating a modulation degree is different from that of the example of discussion. That is, the P0 modulation degree and the P1 modulation degree are defined by the n-th powers of $P_{0,k}/(P_{0,k}+P_{1,k})$ and $P_{1,k}/(P_{0,k}+P_{1,k})$, respectively. Note here that n is a correction coefficient. In the method shown in FIG. 9, these P0 modulation degrees and these P1 modulation degrees are used as detected signals.

Thus, in the first embodiment, the signals that are detected by the respective pixels are corrected by using the signals that are detected by a plurality of close pixels and correction coefficients such as $a_0$, $b_0$, $a_1$, $b_1$, and n. The influence of crosstalk can be canceled by optimizing the correction coefficients. This in turn makes it possible to improve the accuracy of measurement of the degree of coherence or phase of light. A correction coefficient can be determined by using incident light having a known phase difference, such as light having passed through a phase difference plate having a known amount of difference. A correction coefficient needs only be determined so that the P0 modulation degrees and the P1 modulation degrees that are supposed to be obtained from incident light having a known phase difference are equal respectively to the P0 modulation degrees and the P1 modulation degrees calculated from the correction coefficient.

That is, the first embodiment makes it possible to improve the accuracy of measurement of the degree of coherence or phase of light while maintaining the same effects as those of the example of discussion by applying, to the calculation of detected signals, corrections based on signals detected by close pixels.

Further, the first embodiment may be combined with the time-division detection method shown in FIG. 19B. This allows signals captured in a time-division manner to be analyzed in terms of state of coherence. This in turn makes it possible to analyze in more detail the appearance of scattering within the subject.

Second Embodiment

Figure 10:
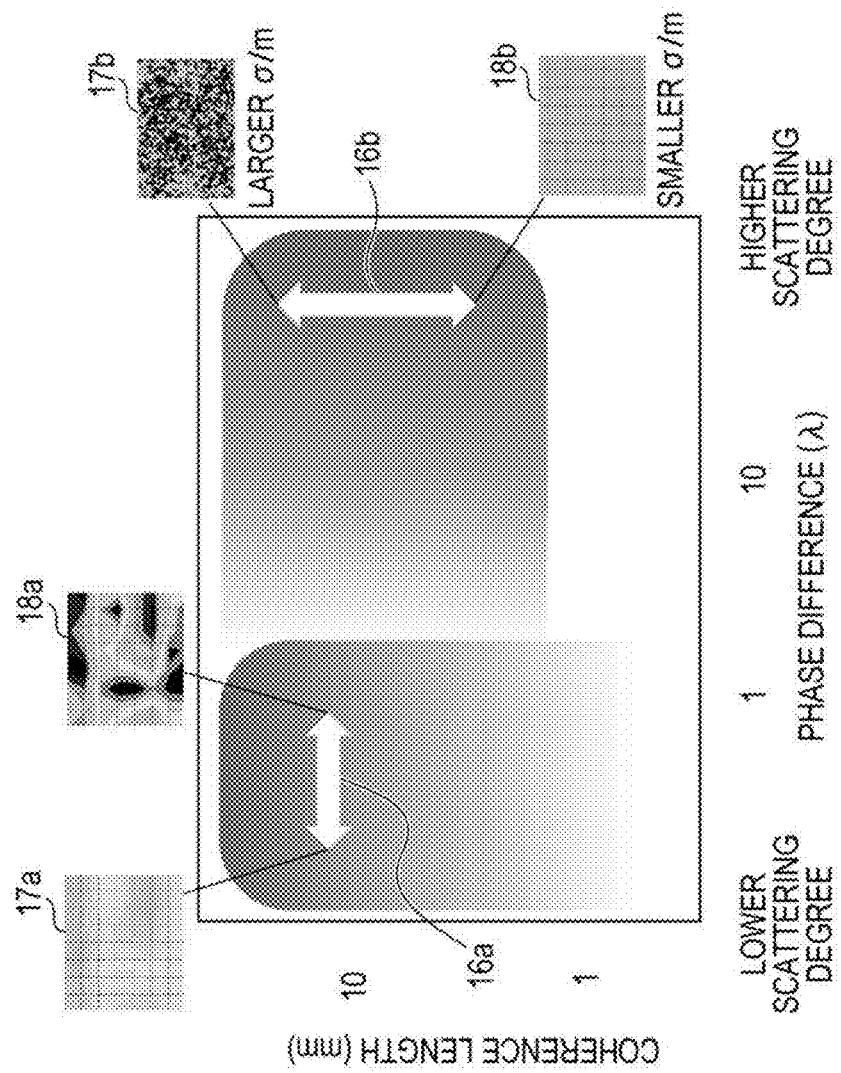
FIG. 10 shows the appearance of detected images with respect to the coherence length of a light source and the phase difference of detected light and a method for signal processing according to a second embodiment.

FIG. 10 shows the states of detected images with respect to the coherence length of a light source and the phase difference of detected light according to a second embodiment. Note, however, that the detected images mean images of P1 modulation degrees and the like. The vertical axis represents the coherence length of the light source, and the horizontal axis represents the phase difference of the detected light in the detector plane. Descriptions are given by taking, as examples, the case of a range 16a where the coherence length of the light source is long and the phase difference is small and the case of a range 16b where the phase difference is large and the coherence length of the light source is variable. As shown in FIG. 1, the phase state of light that is transmitted and reflected by the subject 4 and detected by the photo-detection apparatus 13 varies depending on the subject 4. In the case of a subject such as a thin cell fragment sandwiched between surfaces of metal or flat plates of glass having well-polished surfaces, variations in the phase difference distribution of reflected light or transmitted light that is detected are small.

In the measurement of the range 16a, as described with reference to FIG. 6B (near a=0 on the horizontal axis), the phase of light that is detected is comparatively uniform. In a case where the phase difference of light that is detected is sufficiently smaller than the wavelength of the light that is detected, a detected image 17a is obtained. Meanwhile, in a case where the phase difference of light that is detected is nearly equal to the wavelength of the light that is detected, a detected image 18a is obtained. These detected images 17a and 18a differ in magnitude of detected signals that is expressed by shades of gray of the images. However, the detected images 17a and 18a form designs or patterns of the same kind. In the measurement of the range 16a, the use of the method for signal processing according to the first embodiment makes it possible to cancel the influence of crosstalk and improve the accuracy of measurement. When the scattering degree within the subject 4 is low, the phase difference of light that is detected is small. In this case, the distribution of detected images greatly changes depending on variations in the phase difference of the light that is detected (variations on the horizontal axis in FIG. 10). This makes it possible to find the shape and optical characteristics of the subject 4.

On the other hand, in the measurement of the range 16b, as described with reference to FIG. 6B (near a=1 on the horizontal axis), the phase of light that is detected is almost random. In the case of a short coherence length, a detected images 18b is obtained. In the case of a long coherence length, a detected image 17b is obtained. The detected image 18b is uniform in brightness. The detected image 17b forms a mosaic pattern of mixture of bright portions and dark portions. In the measurement of the range 16b, the standard deviation σ and the average value m are calculated by statistically processing variations among detected signals that are detected within the range of a certain area on the detector. The detected image 18b is small in σ/m. The detected image 17b is large in σ/m. The detection method according to the second embodiment makes it possible to determine an optical difference within a subject by calculating σ/m from signals detected by pixels located in a certain region. When the scattering degree within the subject 4 is high, the phase difference of light that is detected is large. In the second embodiment, the statistical value σ/m greatly changes depending on variations in coherence length (variations on the vertical axis in FIG. 10). This makes it possible to find the structure and optical characteristics of a subject 4 having a high scattering degree.

The region to be statistically processed may be a surface on pixels or a column of pixels along the grating vector direction of the gratings, i.e., the direction of propagation of guided light. In the latter case, the standard deviation σ and the average value m are calculated from a plurality of columns, and the plurality of values of σ, m, σ/m, and the like thus obtained are averaged.

For the purpose of describing the second embodiment, the following describes a relationship between the average and standard deviation of optical path lengths of light emitted after having passed through a subject 4.

Figure 11A:
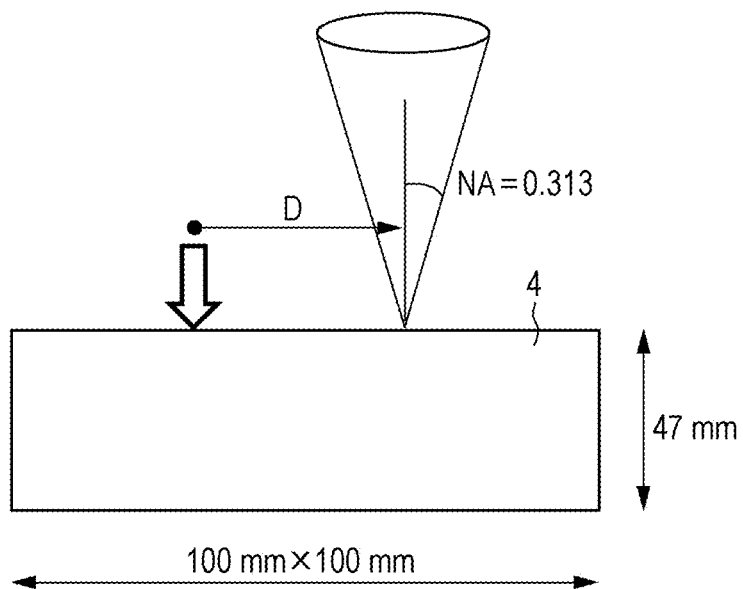
FIG. 11A is a cross-sectional block diagram including a positional relationship between the incidence and emission of light.

FIG. 11A is a cross-sectional block diagram including a positional relationship between the incidence and emission of light. In FIG. 11A, light falls on a flat-plate subject 4 having a thickness of 40 mm. After that, of light emitted from a position that is distant by the distance D from the position of incidence, light that is captured into an aperture of NA=0.313 is detected. The subject 4 used was INO's quasi-biomaterial (Attenuation coefficient $\mu_a$=0.018, Scattering coefficient $\mu_s$=1.58, Anisotropic parameter (g value)= 0.62, Refractive index n=1.52).

Figure 11B:
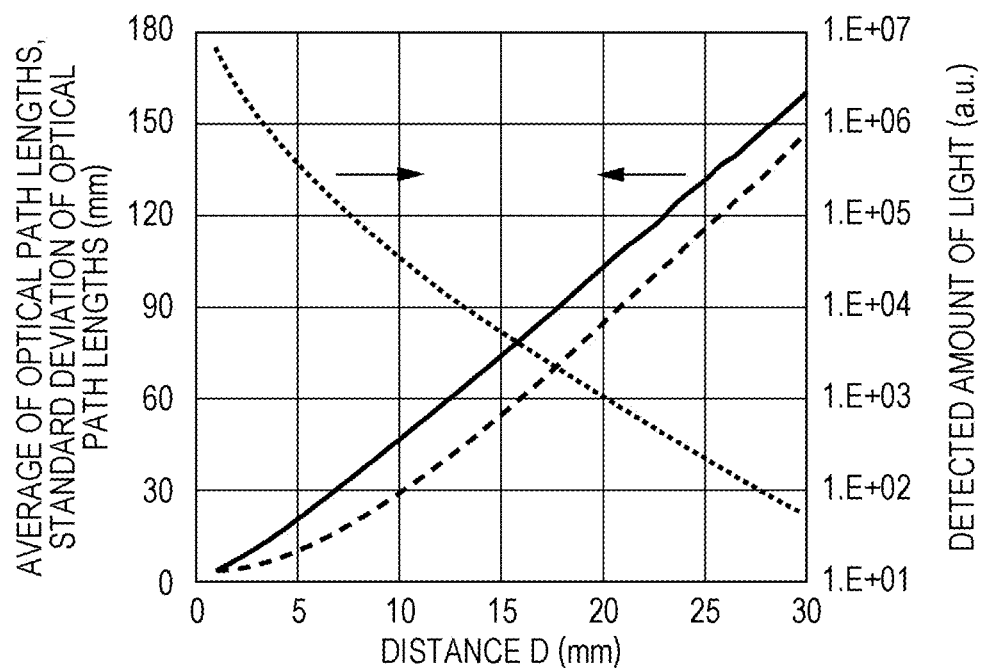
FIG. 11B shows an analysis result obtained with respect to one billion rays of incident light on the basis of a Monte Carlo method in the model of FIG. 11A.

FIG. 11B shows an analysis result obtained with respect to one billion rays of incident light on the basis of a Monte Carlo method in the model of FIG. 11A. The left vertical axis represents the average of optical path lengths and the standard deviation of optical path lengths. The right vertical axis represents the detected amount of light S. The horizontal axis represents the distance D. In FIG. 11B, the solid line, the dashed line, and the dotted line indicate the average optical path length, the optical path length standard deviation, and the detected amount of light, respectively. In a region where D>10 mm, the average and standard deviation of optical path lengths are substantially proportional to each other. The detected amount of light S exponentially decreases with respect to the distance D.

Figure 11C:
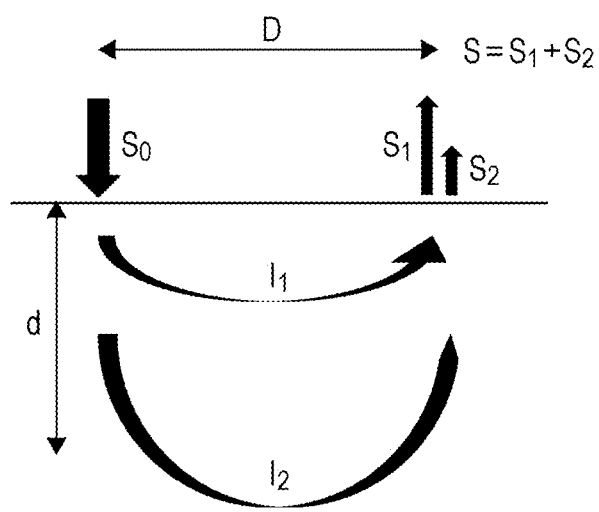
FIG. 11C shows a relationship between the depth of propagation d of a ray of light and the emission intensity.

FIG. 11C shows a relationship between the depth of propagation d of a ray of light and the emission intensity. Let it be assumed that $S_0$ is the amount of incident light that falls on the subject 4 and S is the amount of light that is emitted at a position that is distant by the distance D from the position on which the incident light fell. The amount of light S includes $S_1$ and $S_2$. $S_1$ is the amount of light that is emitted after having propagated the distance of an average length $I_1$ mainly near a surface layer of the subject 4, and $S_2$ is the amount of light that is emitted after having propagated the distance of an average length $I_2$ mainly near a deep layer of the subject 4. Statistically, the optical path length of light that propagates near the surface layer is shorter than the optical path length of light that propagates near the deep layer ($I_1$<$I_2$). Therefore, in a case where there is absorption in the subject ($\mu_a$>0), $S_1$>$S_2$. The ratio between $S_1$ and $S_2$ changes depending on the optical constant of the subject. The average and standard deviation of optical path lengths of emitted light also change depending on the optical constant of the subject.

Figure 11D:
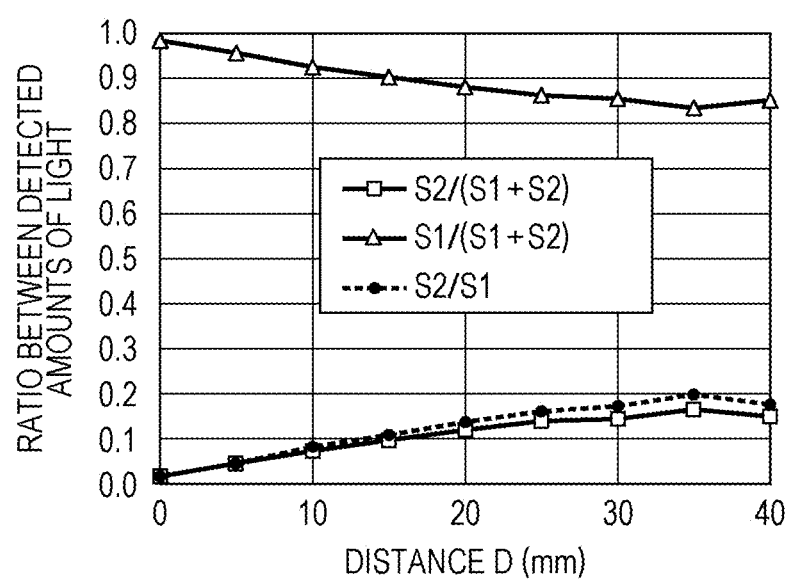
FIG. 11D shows an analysis result based on the Monte Carlo method for explaining the relationship between the depth of propagation d and the emission intensity.

FIG. 11D shows an analysis result based on the Monte Carlo method for explaining the relationship between the depth of propagation d and the emission intensity. $S_1$ is the amount of light that is emitted after having propagated through the surface layer at the depth of propagation d (the range of d=0 to 7 mm). $S_2$ is the amount of light that is emitted after having propagated through the deep layer at the depth of propagation d (the range of d=7 to 47 mm). In FIG. 11D, the triangles, the quadrangles, and the black circles indicate the ratio between amounts of light $S_1/(S_1+S_2)$, the ratio between amounts of light $S_2/(S_1+S_2)$, and the ratio between the amounts of light $S_2/S_1$, respectively. FIG. 11D shows that the ratio between the amounts of light $S_2/S_1$ changes according to the distance D and reaches its maximum at approximately D=35 mm. That is, there is a certain degree of correlation between variations in optical path length difference and the depth of propagation d.

In the conventional technology, changes in detected images have been examined by changing the amount of light that falls on a subject 4. However, even with the use of such changes in amount of light, it has been difficult to find information on optical path lengths and depths of propagation. Meanwhile, in the second embodiment, the optical path length can be estimated by calculating σ/m, which indicates variations in optical path length. Furthermore, by changing the coherence length, changes in σ/m can be analyzed and information on depths of propagation and an internal optical structure can be found.

The following describes differences in the appearance of detected signals in the second embodiment.

Figure 12A:
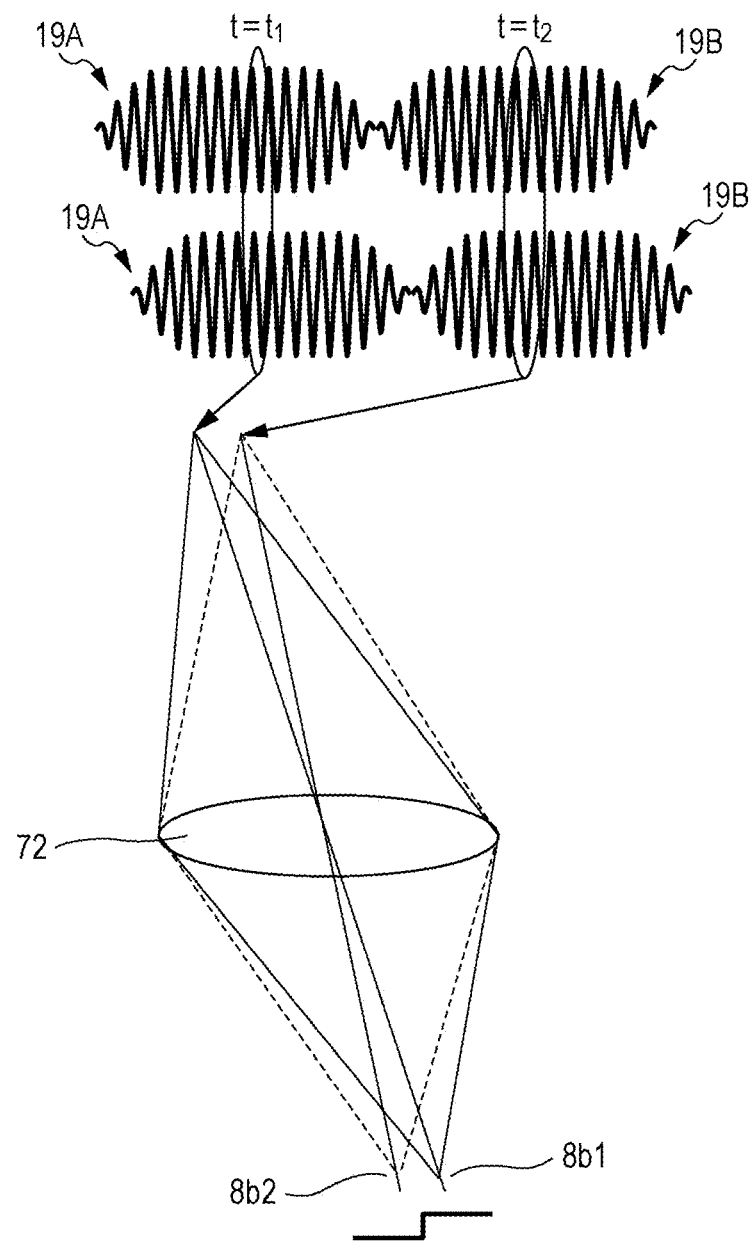
FIG. 12A shows a case of detection of two identical wave packets that are out of phase with each other.

FIG. 12A shows a case of detection of two wave packets 19A that are out of phase with each other. The wave packets 19A are followed by wave packets 19B having the same coherence length as each other and having no phase correlation with each other. At a point in time t=$t_1$, those waveforms of the two wave packets 19A which fall in a range surrounded by an ellipse are captured by a lens 72 to form an image 8b1 on the detector plane of the photodetector. At a point in time t=$t_2$, those waveforms of the two wave packets 19B which fall in a range surrounded by an ellipse are captured by the lens 72 to form an image 8b2 on the detector plane of the photodetector. The images 8b1 and 8b2 have no phase correlation with each other. However, since the images 8b1 and 8b2 are both interfering light of the same wave packets, the phase distribution does not change even when the point in time t changes from $t_1$ to $t_2$. The detected images 17a and 18a in the range 16a in FIG. 10 are equivalent to the case of FIG. 12A.

Figure 12B:
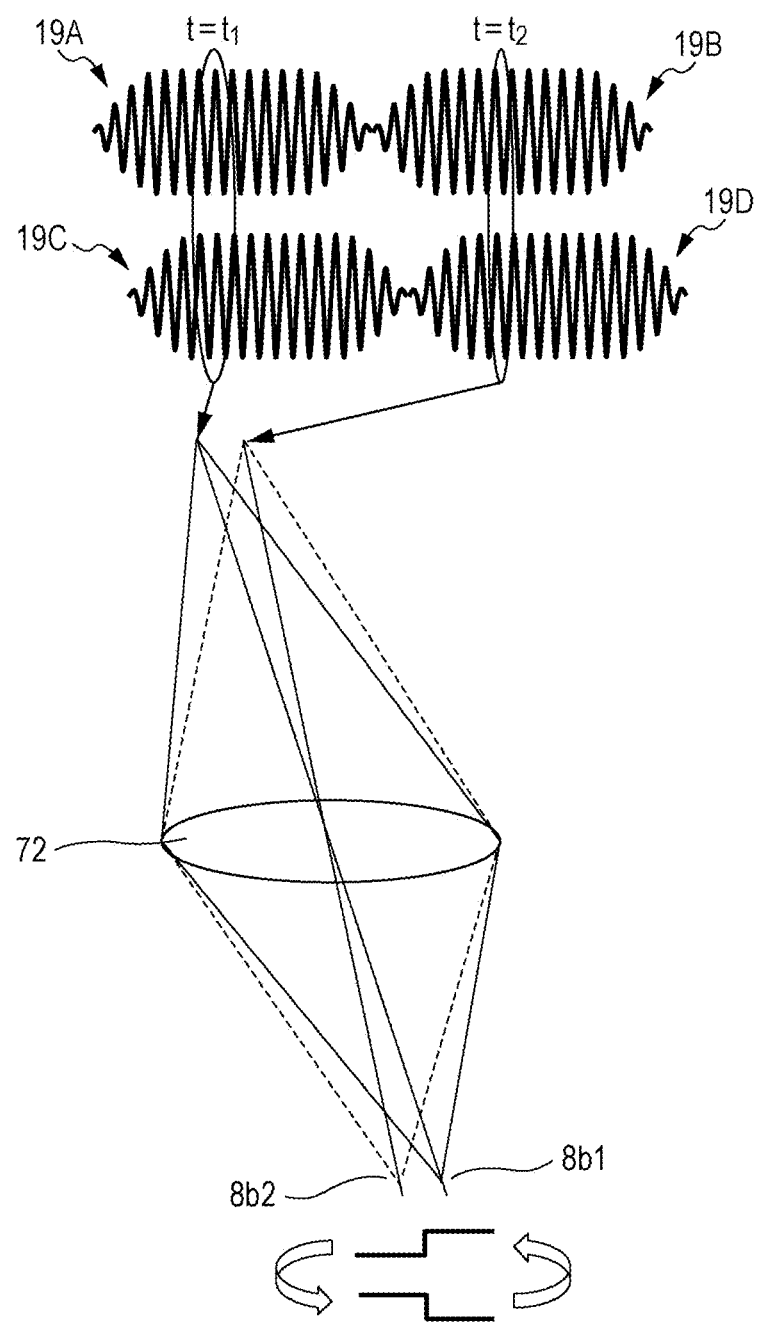
FIG. 12B shows a case of detection of wave packets of the same wavelength and different phases.

FIG. 12B shows a case of detection of wave packets 19A and 19C of the same wavelength and different phases. The wave packets 19A and 19C are followed by wave packets 19B and 19D having the same coherence length as each other and having no phase correlation with each other, respectively. At the point in time t=$t_1$, those waveforms of the two wave packets 19A and 19C which fall in a range surrounded by an ellipse are captured by the lens 72 to form an image 8b1 on the detector plane of the photodetector. The different wave packets 19A and 19C thus captured have no phase correlation with each other. At the point in time t=$t_2$, those waveforms of the two wave packets 19B and 19D which fall in a range surrounded by an ellipse are captured by the lens 72 to form an image 8b2 on the detector plane of the photodetector. The different wave packets 19B and 19D thus captured have no phase correlation with each other, either. The images 8b1 and 8b2 have no phase correlation with each other. Further, since the images 8b1 and 8b2 are interfering light of different wave packets, the phase distribution changes when the point in time t changes from $t_1$ to $t_2$. That is, the phase distribution is temporally unstable. The detected images 17b and 18b in the range 16b in FIG. 10 are equivalent to the case of FIG. 12B.

A light-emitting apparatus that is used in the second embodiment is described. The light-emitting apparatus includes a light source 2A that emits light in a wavelength range centered at the wavelength $\lambda_0$ and a light source 2B that emits light in a wavelength range whose center is located near the wavelength $\lambda_0$. The light source 2B is temperature-controlled, for example, by a Peltier element. The light source 2B can control a wavelength difference between the light sources 2A and 2B by utilizing changes in temperature. The light emitted from the light source 2A and the light emitted from the light source 2B are multiplexed by an optical multiplexer to form mixed light. Alternatively, simultaneous irradiation of a scattering subject with the light emitted from the light source 2A and the light emitted from the light source 2B effect scattering light mixing, so that the mixed light thus multiplexed can be detected on the detecting side.

Figure 13A:
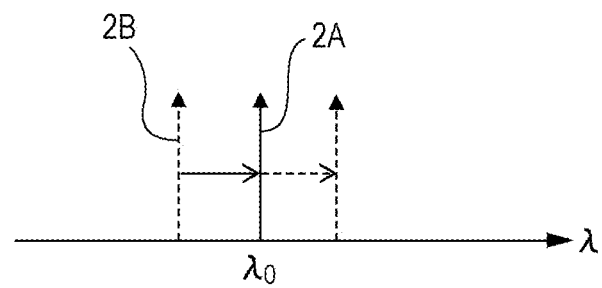
FIG. 13A shows the way in which the wavelength of a first light source crosses the wavelength $\lambda_0$ of a second light source by being changed by changing the temperature of the first light source with a Peltier element.

FIG. 13A shows the way in which raising the temperature of the light source 2B with the Peltier element causes the wavelength of light that is emitted from the light source 2B to change in such a way as to cross the wavelength $\lambda_0$ of light that is emitted from the light source 2A. As described with reference to FIG. 18E, the period of a beat that is generated by interference between two rays of light with a wavelength difference $\Delta\lambda$ is $\lambda_0^2/\Delta\lambda$, which is the coherence length of the mixed light.

Figure 13B:
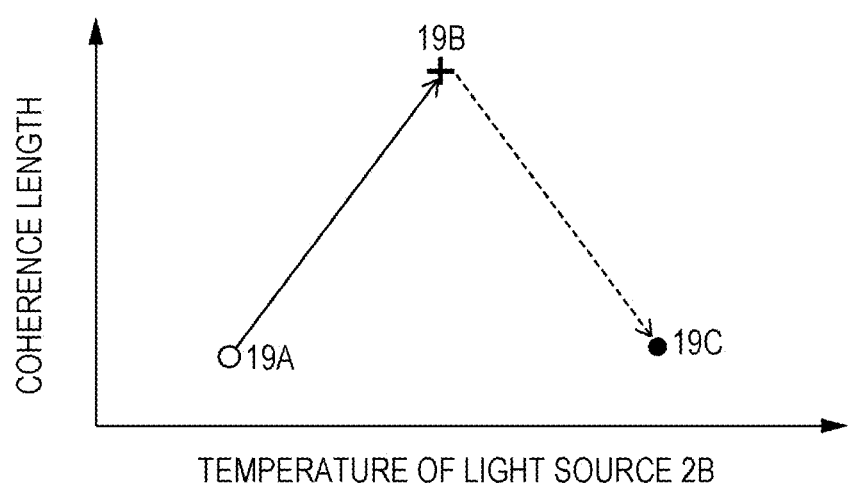
FIG. 13B shows changes in coherence length with respect to changes in temperature of the first light source.

FIG. 13B shows changes in coherence length of mixed light with respect to changes in temperature of the light source 2B based on this principle. The coherence length of the mixed light becomes longer as the temperature becomes higher (state from the point 19A to the point 19B). The coherence length of the mixed light reaches its maximum as soon as the wavelength difference between the two light sources vanishes (state at the point 19B). The coherence length of the mixed light becomes shorter as the temperature becomes further higher (state from the point 19B to the point 19C). Lowering the temperature to the contrary causes a reverse process to proceed. In general, in the case of a light source such as a semiconductor laser, wavelength changes with temperature. Therefore, it is difficult to fix the wavelength at a constant value. However, use of a method for controlling a light-emitting apparatus according to the second embodiment makes it possible to effect, in a measurable time range, a change from a state where the coherence length is short to a state where the coherence length is long and a change from the state where the coherence length is long to a state where the coherence length is short. As a result, the method can be used in the measurement in the range 16b in FIG. 10.

That is, in the second embodiment, the standard deviation, the average value, and the ratio therebetween are calculated by statistically processing signal variations among detected signals that are detected within the range of a certain area on the photodetector. This makes it possible to, while maintaining the same effects as those of the example of discussion, measure variations in the degrees of coherence or phases of light in a case where the subject is a scattering body. Further, the variability of the coherence length, which is needed for measurements, can be more easily achieved by controlling the temperature of a light source.

Third Embodiment

Figure 20A:
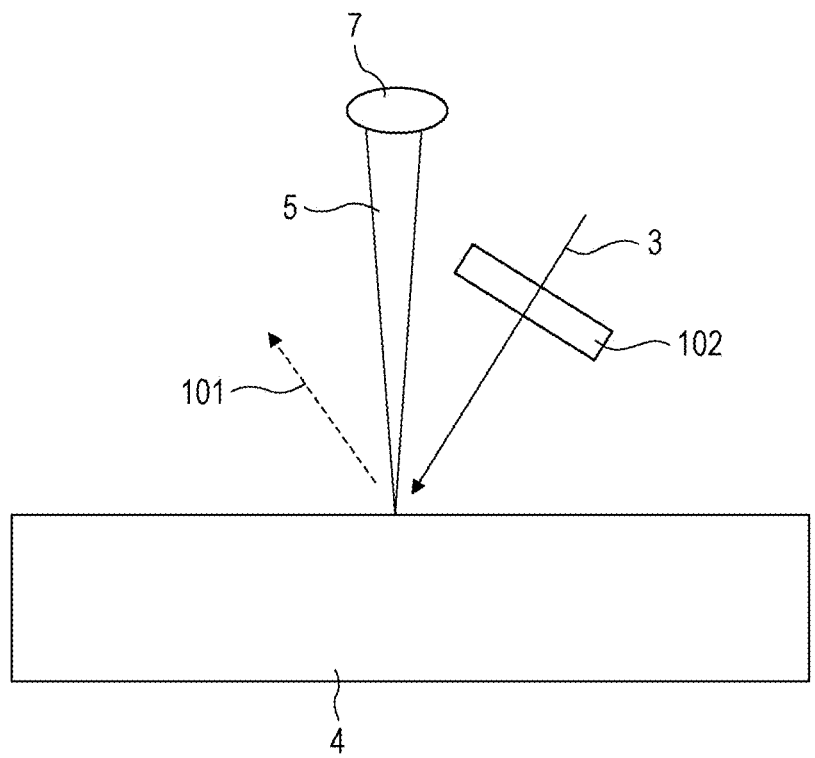
FIG. 20A shows a positional relationship between incident light, reflected light, and detected light with respect to a subject in a photo-detection apparatus according to a third embodiment.

A photo-detection apparatus according to a third embodiment is described with reference to FIGS. 20A to 20C. In the photo-detection apparatus according to the third embodiment, a positional relationship between the directions of incidence, reflection, and detection of light 3 with respect to a subject 4 is set as shown in FIG. 20A. The direction of the lens optical system 7 with respect to the subject 4 lies between the direction of incidence of the light 3 and the direction of emission of reflected light 101, and scattering light 5 shown in FIG. 20A falls on the lens optical system 7. A photo-detection apparatus that detects light having traveled through the lens optical system 7 is omitted as it is the same as that of another embodiment. A half-wavelength plate 102 is disposed on the optical path of the light 3. Rotating the direction of linear polarization with the half-wavelength plate 102 allows the direction of polarization of the light 3 to be set to either of two directions that are orthogonal to each other, namely a TE direction and a TM direction. Further, in FIG. 20B, an analyzer 103 is disposed right in front of the lens optical system 7 in order to evaluate the performance of the photo-detection apparatus according to the third embodiment. The analyzer 103 selectively transmits either light in the TE direction or light in the TM direction. That is, the half-wavelength plate 102 makes it possible to switch the direction of polarization of incident light between the TE direction and the TM direction. Further, the analyzer 103 makes it possible to selectively detect either light that is polarized in the TE direction and light that is polarized in the TM direction.

Figure 20B:
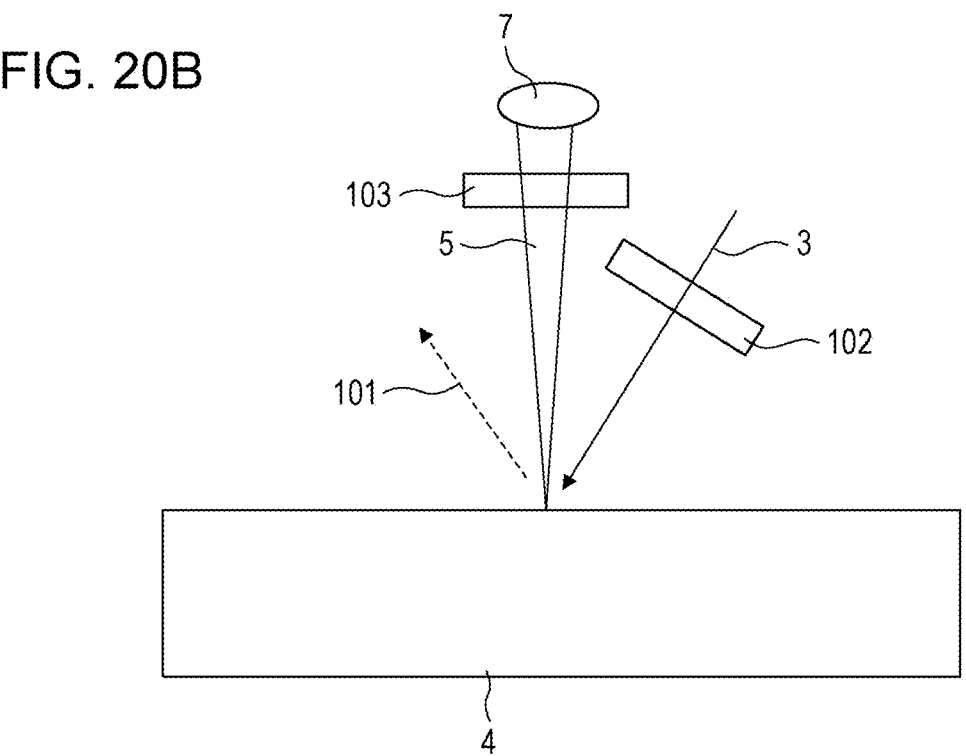
FIG. 20B shows a system of measurement for evaluating the performance of the photo-detection apparatus according to the third embodiment.
Figure 20C:
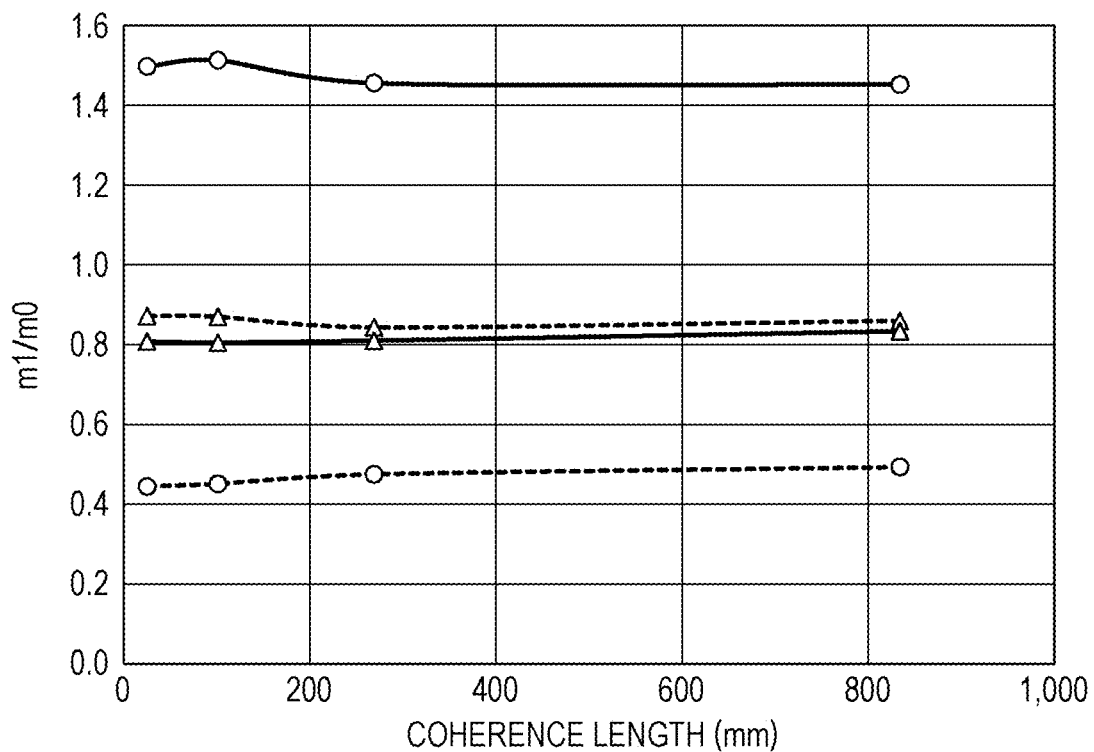
FIG. 20C shows results of measurements performed under conditions where the direction of polarization of incident light and the direction of polarization of detected light are orthogonal to each other according to the third embodiment.
Figure 20D:
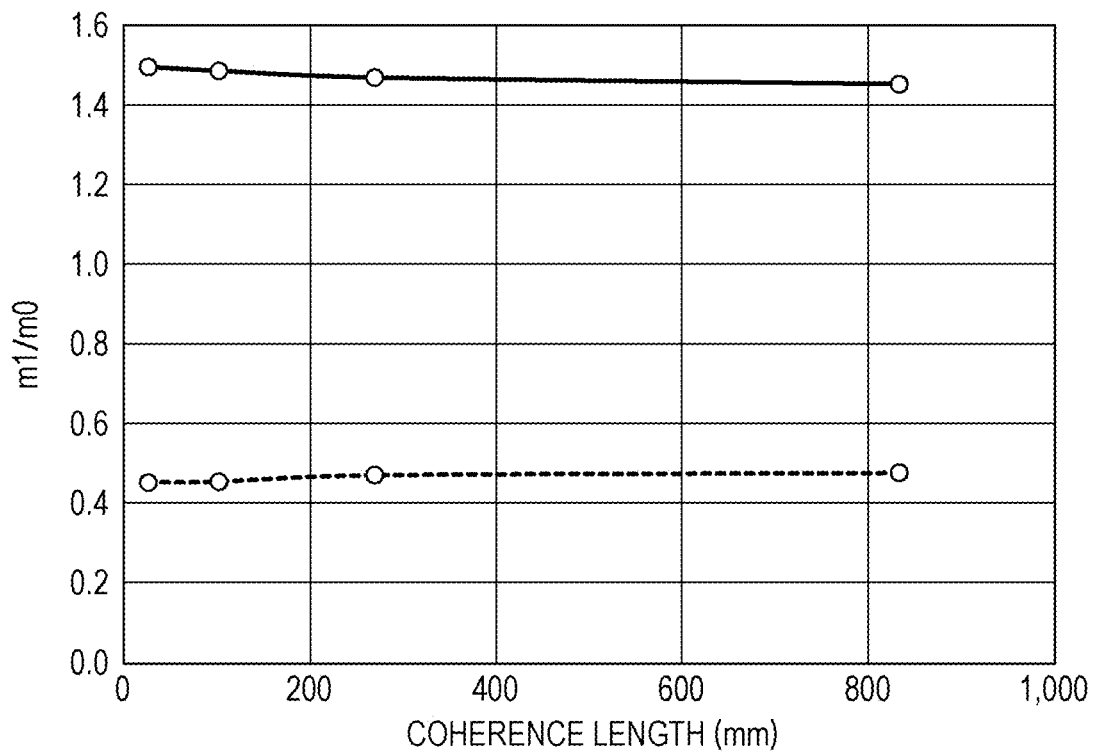
FIG. 20D shows results of measurements performed under conditions where the direction of polarization of incident light and the direction of polarization of detected light are parallel to each other according to the third embodiment.

FIG. 20C shows results of measurements performed under conditions where the direction of polarization of incident light and the direction of polarization of detected light are orthogonal to each other under the conditions of FIG. 20B. FIG. 20D shows results of measurements performed under conditions where the direction of polarization of incident light and the direction of polarization of detected light are parallel to each other. In each of FIGS. 20C and 20D, the vertical axis represents the ratio m1/m0 between the average m1 of P1 modulation degrees and the average m0 of P0 modulation degrees, and the horizontal axis represents the coherence length of the light 3 from the light source 2. In FIG. 20C, white circles and a solid line indicate the results of measurements performed in a case where the direction of polarization of the incident light is the TM direction and the light in the TE direction is detected, white circles and a dashed line indicate the results of measurements performed in a case where the direction of polarization of the incident light is the TE direction and the light in the TM direction is detected, triangles and a solid line indicate the results of measurements performed in a case where the direction of polarization of the incident light is the TM direction and the analyzer 103 is removed, i.e. a case where light of total polarization (TEM) is detected, and triangles and a dashed line indicate the results of measurements performed in a case where the direction of polarization of the incident light is the TE direction and the light of total polarization is detected. As shown in FIG. 20C, m1/m0 takes on a value of approximately 1.4 to 1.5 in a case where the direction of polarization of the incident light is the TM direction and the light in the TE direction is detected. Meanwhile, m1/m0 takes on a value of approximately 0.4 to 0.5 in a case where the direction of polarization of the incident light is the TE direction and the light in the TM direction is detected. Further, m1/m0 takes on a value of approximately 0.8 in both a case where the direction of polarization of the incident light is the TM direction and the light of total polarization is detected and a case where the direction of polarization of the incident light is the TE direction and the light of total polarization is detected. In FIG. 20D, white circles and a solid line indicate the results of measurements performed in a case where the direction of polarization of the incident light is the TE direction and the light in the TE direction is detected, and white circles and a dashed line indicate the results of measurements performed in a case where the direction of polarization of the incident light is the TM direction and the light in the TM direction is detected. As shown in FIG. 20D, m1/m0 takes on a value of approximately 1.4 to 1.5 in a case where the direction of polarization of the incident light is the TE direction and the light in the TE direction is detected, whereas m1/m0 takes on a value of approximately 0.4 to 0.5 in a case where the direction of polarization of the incident light is the TM direction and the light in the TM direction is detected.

FIGS. 20C and 20D show that although m1/m0 takes on a value of approximately 0.8 in a case where the detected light contains TE and TM components in equal proportions, containing more of the TM component makes the value smaller and containing more of the TE component makes the value larger. This makes it possible to determine the degree of polarization of the detected light on the basis of the magnitude of m1/m0.

As described above, the photo-detection apparatus according to the third embodiment calculates the ratio between the average values by statistically processing signal variations among detected signals that are detected within the range of a certain area on the photodetector. Specifically, the average m1 of P1 modulation degrees and the average m0 of P0 modulation degrees within the range of a certain area on the photodetector are calculated, and furthermore, the ratio m1/m0 between the averages m1 and m0 is calculated. This makes it possible to measure the degree of polarization of scattering light in a case where the subject is a scattering body.

The first to third embodiments have been described above with reference to a case where the light 3 that is emitted from the light source 2 has one wavelength. Alternatively, detected signals with respect to light 3 having a plurality of different wavelengths may be detected either simultaneously or in a time-division manner. In this case, there is an advantage in that information on the inside of a subject can be more accurately detected. Applied examples of cases of use of light 3 of a plurality of wavelengths are shown in FIGS. 14A to 15B.

Figure 14A:
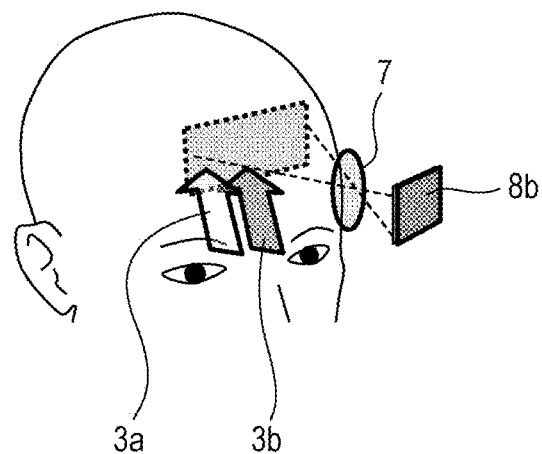
FIG. 14A is a diagram showing an example of a system that detects concentration distributions of oxyhemoglobin and deoxyhemoglobin in cerebral blood flow.

FIG. 14A shows an example of a system that more accurately detects concentration distributions of oxyhemoglobin (O-Hb) and deoxyhemoglobin (D-Hb) in cerebral blood flow. In this example, the head of a human is irradiated with a first emitted light 3a of a wavelength $\lambda_1$ and a second emitted light 3b of a wavelength $\lambda_2$, and an image 8b is detected by the photo-detection apparatus through the lens optical system 7.

Oxyhemoglobin and deoxyhemoglobin are greatly absorbed at different wavelengths, respectively. For example, at a wavelength of 750 nm, deoxyhemoglobin has a greater absorption coefficient than oxyhemoglobin. At a wavelength of 850 nm, the opposite is true.

Figure 14B:
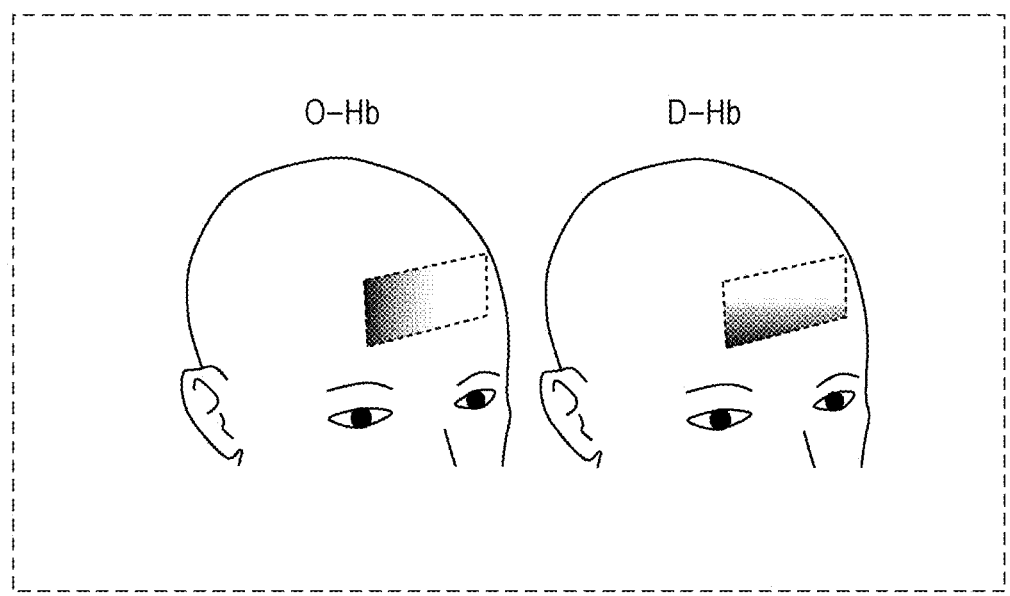
FIG. 14B is a diagram schematically showing concentration distributions of oxyhemoglobin and deoxyhemoglobin in cerebral blood flow.

FIG. 14B is a diagram schematically showing, in regions surrounded by dotted lines, concentration distributions of oxyhemoglobin and deoxyhemoglobin in cerebral blood flow. The first emitted light 3a of the wavelength $\lambda_1=750$ nm and the second emitted light 3b of the wavelength $\lambda_2=850$ nm are used, and statistical processing is performed on detected signals obtained with respect to the respective wavelengths. This makes it possible to more accurately measure such concentration distributions of O-Hb and D-Hb in cerebral blood flow as those shown in FIG. 14B than in a case where emitted light having one wavelength is used.

Figure 15A:
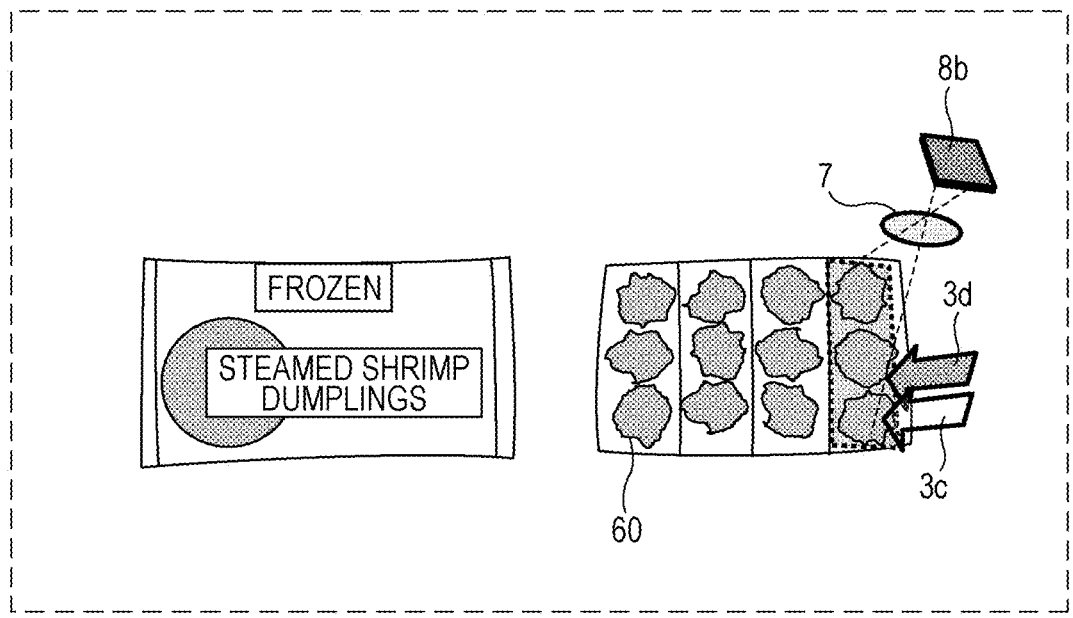
FIG. 15A is a diagram showing an example of a system that detects foreign matter contaminating food.

FIG. 15A is a diagram showing an example of a system that detects foreign matter contaminating food. In this example, food 60 is irradiated with emitted light 3c of a wavelength $\lambda_3$ and emitted light 3d of a wavelength $\lambda_4$, and an image 8b is detected by the photo-detection apparatus through the lens optical system 7.

The food 60 is constituted by components such as carbon hydrate, fat, moisture, and protein that have their respective unique absorption wavelengths of near-infrared light or visible light. Further, foreign matter 70 that may contaminate the food 60, such as a piece of metal or a strand of hair, has absorption characteristics which are different from those of the components of the food 60.

Figure 15B:
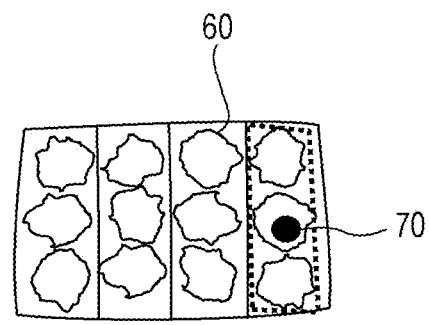
FIG. 15B is a diagram explaining a state of contamination of food with foreign matter.

FIG. 15B is a diagram explaining a state of contamination of food with foreign matter. The emitted light 3c of the wavelength $\lambda_3$ and the emitted light $3d$ of the wavelength $\lambda_4$ are used, and statistical processing is performed on detected signals obtained with respect to the respective wavelengths. This makes it possible to more accurately detect such foreign matter 70 present in the food 60 as that shown in FIG. 15B than in a case where emitted light having one wavelength is used. The wavelengths of emitted light used here may be matched to two absorption wavelengths unique to the food 60, which is a subject, instead of being matched to the absorption wavelength of the foreign matter 70.

As described above, the present disclosure encompasses aspects described in the following items.

[Item 1] A photo-detection system according to Item 1 of the present disclosure includes: a photo-detection apparatus; and an arithmetic circuit, the photo-detection apparatus including a light-shielding film including light-transmitting regions and light-shielding regions, the light-transmitting regions and the light-shielding regions being alternately arranged in at least a first direction within a plane, an optically-coupled layer facing the light-shielding film, the optically-coupled layer including a grating which generates a propagating light that propagates in the first direction and a transmitting light that transmits the optically-coupled layer when incident light of a predetermined wavelength enters the light-transmitting regions, and a photodetector having an imaging area, the photodetector including first photo-detection cells and second photo-detection cells, the first photo-detection cells and the second photo-detection cells being arranged on the imaging area, each of the first photo-detection cells corresponding to at least one of the light-transmitting regions, each of the second photo-detection cells corresponding to at least one of the light-shielding regions, and the arithmetic circuit generating, based on first signals that are obtained from the first photo-detection cells and second signals that are obtained from the second photo-detection cells, third signals each representing coherence of light having entered a position of each of the first and second photo-detection cells, the arithmetic circuit generating at least one selected from the group consisting of an average value of the third signals, a standard deviation of the third signals, a ratio between the standard deviation and the average value, and a ratio between an average value of a first portion of the third signals and an average value of a second portion of the third signals in positions of at least a part of the first photo-detection cells and the second photo-detection cells that are included in a region of the imaging plane. The first portion of the third signals is based on light having entered the positions of the first photo-detection cells, and the second portion of the third signals is based on light having entered the positions of the second photo-detection cells.

[Item 2] In the photo-detection system according to Item 1, the arithmetic circuit may generate, as the third signals corresponding to the first photo-detection cells, signals that are obtained by an operation $P_1'(P_0+P_1')$, $P_0/(P_0+P_1')$ or $P_1'/P_0$, and generate, as the third signals corresponding to the second photo-detection cells, signals that are obtained by an operation $P_1/(P_0'+P_1)$, $P_0'/(P_0'+P_1)$ or $P_1/P_0'$, where $P_0$ is each of the first signals, $P_1$ is each of the second signals, $P_1'$ is an average value of two signals that are obtained from two of the second photo-detection cells which are adjacent to each of the first photo-detection cells in the first direction and a direction opposite to the first direction, and $P_0'$ is an average value of two signals that are obtained from two of the first photo-detection cells which are adjacent to each of the second photo-detection cells in the first direction and the direction opposite to the first direction.

[Item 3] In the photo-detection system according to Item 1 or 2, the optically-coupled layer may further include:

a first low-refractive-index layer, a first high-refractive-index layer disposed on the first low-refractive-index layer and including the grating, and a second low-refractive-index layer disposed on the first high-refractive-index layer, and the first high-refractive-index layer may have a higher refractive index than the first low-refractive-index layer and the second low-refractive-index layer.

[Item 4] In the photo-detection system according to any of Items 1 to 3, the photodetector may further include:

first microlenses each disposed on a corresponding one of the first photo-detection cells, and second microlenses each disposed on a corresponding one of the second photo-detection cells.

[Item 5] A photo-detection system according to Item 5 of the present disclosure includes:

a photo-detection apparatus; and an arithmetic circuit, the photo-detection apparatus including a light-shielding film including light-transmitting regions and light-shielding regions, the light-transmitting regions and the light-shielding regions being alternately arranged in at least a first direction within a plane, an optically-coupled layer facing the light-shielding film, the optically-coupled layer including a grating which generates a propagating light that propagates in the first direction and a transmitting light that transmits the optically-coupled layer when incident light of a predetermined wavelength enters the light-transmitting regions, and a photodetector having an imaging area, the photodetector including first photo-detection cells and second photo-detection cells, the first photo-detection cells and the second photo-detection cells being arranged on the imaging area, each of the first photo-detection cells corresponding to at least one of the light-transmitting regions, each of the second photo-detection cells corresponding to at least one of the light-shielding regions, and the arithmetic circuit correcting each of first signals that are obtained from at least part of the first photo-detection cells by using two of the first signals that are obtained from two of the first photo-detection cells located closest in the first direction and a direction opposite to the first direction to each of the at least part of the first photo-detection cells, the arithmetic circuit correcting each of second signals that are obtained from at least part of the second photo-detection cells by using two of the second signals that are obtained from two of the second photo-detection cells located closest in the first direction and the direction opposite to the first direction to each of the at least part of the second photo-detection cells, the arithmetic circuit outputting, based on the first signals thus corrected and the second signals thus corrected, third signals each representing coherence of light having entered a position of each of the first and second photo-detection cells.

[Item 6] In the photo-detection system according to Item 5, the arithmetic circuit may correct each of the first signals by further using two of the first signals that are obtained from two of the first photo-detection cells located second closest in the first direction and the direction opposite to the first direction to each of the at least part of the first photo-detection cells, and the arithmetic circuit may correct each of the second signals by further using two of the second signals that are obtained from two of the second photo-detection cells located second closest in the first direction and the direction opposite to the first direction to each of the at least part of the second photo-detection cells.

[Item 7] In the photo-detection system according to Item 5 or 6, the arithmetic circuit may generate, as the third signals corresponding to the at least part of the first photo-detection cells, signals that are obtained by an operation $P_1'/(P_0+P_1')$, $P_0/(P_0+P_1')$ or $P_0'/P_0$, and generate, as the third signals corresponding to the at least part of the second photo-detection cells, signals that are obtained by an operation $P_1/(P_0'+P_1)$, $P_0'/(P_0'+P_1)$ or $P_1/P_0'$, where $P_0$ is each of the first signals thus corrected, $P_1$ is each of the second signals thus corrected, $P_1'$ is an average value of two signals that are obtained from two of the second photo-detection cells which are adjacent to each of the at least part of the first photo-detection cells in the first direction and the direction opposite to the first direction, and $P_0'$ is an average value of two signals that are obtained from two of the first photo-detection cells which are adjacent to each of the at least part of the second photo-detection cells in the first direction and the direction opposite to the first direction.

[Item 8] In the photo-detection system according to any of Items 5 to 7, the optically-coupled layer may further include:
a first low-refractive-index layer,
a first high-refractive-index layer disposed on the first low-refractive-index layer and including the grating, and
a second low-refractive-index layer disposed on the first high-refractive-index layer, and
the first high-refractive-index layer may have a higher refractive index than the first low-refractive-index layer and the second low-refractive-index layer.

[Item 9] In the photo-detection system according to any of Items 5 to 8, the photodetector may further include:
first microlenses each disposed on a corresponding one of the first photo-detection cells, and
second microlenses each disposed on a corresponding one of the second photo-detection cells.

[Item 10] A light-emitting apparatus according to Item 10 of the present disclosure includes:
a first light source that emits a first coherent light having a first wavelength;
a second light source that emits a second coherent light having a second wavelength that, with changes in temperature of the second light source, varies within a wavelength range including the first wavelength; and
an optical multiplexer that multiplexes the first coherent light and the second coherent light.

[Item 11] A non-transitory computer readable medium according to Item 11 of the present disclosure, the non-transitory computer readable medium storing a program for processing signals that are outputted from the photodetector of the photo-detection system according to any of Items 1 to 4, the program causing a processor to generate, based on first signals that are obtained from the first photo-detection cells and second signals that are obtained from the second photo-detection cells, third signals each representing coherence of light having entered a position of each of the first and second photo-detection cells, the program causing the processor to generate at least one selected from the group consisting of an average value of the third signals, a standard deviation of the third signals, a ratio between the standard deviation and the average value, and a ratio between an average value of a first portion of the third signals and an average value of a second portion of the third signals in positions of at least a part of the first photo-detection cells and the second photo-detection cells that are included in a region of the imaging plane. The first portion of the third signals is based on light having entered the positions of the first photo-detection cells, and the second portion of the third signals is based on light having entered the positions of the second photo-detection cells.

[Item 12] A non-transitory computer readable medium according to Item 12 of the present disclosure, the non-transitory computer readable medium storing a program for processing signals that are outputted from the photodetector of the photo-detection system according to any of Items 5 to 9, the program causing a processor to correct each of first signals that are obtained from at least part of the first photo-detection cells by using two of the first signals that are obtained from two of the first photo-detection cells located closest in the first direction and a direction opposite to the first direction to each of the at least part of the first photo-detection cells, the program causing the processor to correct each of second signals that are obtained from at least part of the second photo-detection cells by using two of the second signals that are obtained from two of the second photo-detection cells located closest in the first direction and the direction opposite to the first direction to each of the at least part of the second photo-detection cells, the program causing the processor to output, based on the first signals thus corrected and the second signals thus corrected, third signals each representing coherence of light having entered a position of each of the first and second photo-detection cells.

[Item 13] In non-transitory computer readable medium according to Item 12, the processor may be caused to correct each of the first signals by further using two of the first signals that are obtained from two of the first photo-detection cells located second closest in the first direction and the direction opposite to the first direction to each of the at least part of the first photo-detection cells, and the processor may be caused to correct each of the second signals by further using two of the second signals that are obtained from two of the second photo-detection cells located second closest in the first direction and the direction opposite to the first direction to each of the at least part of the second photo-detection cells.

[Item 14] In the photo-detection system according to any of Items 1 to 4, the photo-detection system may further include the light-emitting apparatus according to Item 10, and the photo-detection system may irradiate a subject with light emitted from the light-emitting apparatus and detect light having returned the subject.

[Item 15] A method according to Item 15 of the present disclosure includes:

by using a first light source that emits a first coherent light having a first wavelength and a second light source that emits a second coherent light having a second wavelength, simultaneously irradiating a subject with the first coherent light and the second coherent light and thereby multiplexing the first coherent light and the second coherent light to obtain multiplexed light; and changing the coherence length of the multiplexed light by changing the temperature of the second light source to cause the second wavelength to vary within a wavelength range including the first wavelength.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

What is claimed is:

1. A photo-detection system comprising:
   a photo-detection apparatus; and
   an arithmetic circuit,
   the photo-detection apparatus including:
      a light-shielding film including light-transmitting regions and light-shielding regions, the light-transmitting regions and the light-shielding regions being alternately arranged in at least a first direction within a plane,
      an optically-coupled layer facing the light-shielding film, the optically-coupled layer including a grating which generates a propagating light that propagates in the first direction and a transmitting light that transmits the optically-coupled layer when incident light of a predetermined wavelength enters the light-transmitting regions, and
      a photodetector having an imaging area, the photodetector including first photo-detection cells and second photo-detection cells, the first photo-detection cells and the second photo-detection cells being arranged on the imaging area, each of the first photo-detection cells corresponding to at least one of the light-transmitting regions, each of the second photo-detection cells corresponding to at least one of the light-shielding regions, and
   the arithmetic circuit generating, based on first signals that are obtained from the first photo-detection cells and second signals that are obtained from the second photo-detection cells, third signals each representing coherence of light having entered a position of each of the first and second photo-detection cells,
   the arithmetic circuit generating at least one selected from the group consisting of an average value of the third signals, a standard deviation of the third signals, a ratio between the standard deviation and the average value, and a ratio between an average value of a first portion of the third signals and an average value of a second portion of the third signals in positions of at least a part of the first photo-detection cells and the second photo-detection cells that are included in a region of the imaging plane, wherein:
   the first portion of the third signals is based on light having entered the positions of the first photo-detection cells, and
   the second portion of the third signals is based on light having entered the positions of the second photo-detection cells.

2. The photo-detection system according to claim 1, wherein the arithmetic circuit generates, as the third signals corresponding to the first photo-detection cells, signals that are obtained by an operation $P_1'/(P_0+P_1')$, $P_0/(P_0+P_1')$ or $P_1'/P_0$, and generates, as the third signals corresponding to the second photo-detection cells, signals that are obtained by an operation $P_1/(P_0'+P_1)$, $P_0'/(P_0'+P_1)$ or $P_1/P_0'$,
   where $P_0$ is each of the first signals,
   $P_1$ is each of the second signals,
   $P_1'$ is an average value of two signals that are obtained from two of the second photo-detection cells which are adjacent to each of the first photo-detection cells in the first direction and a direction opposite to the first direction, and
   $P_0'$ is an average value of two signals that are obtained from two of the first photo-detection cells which are adjacent to each of the second photo-detection cells in the first direction and the direction opposite to the first direction.

3. The photo-detection system according to claim 1, wherein the optically-coupled layer further includes:
   a first low-refractive-index layer,
   a first high-refractive-index layer disposed on the first low-refractive-index layer and including the grating, and
   a second low-refractive-index layer disposed on the first high-refractive-index layer, and
   the first high-refractive-index layer has a higher refractive index than the first low-refractive-index layer and the second low-refractive-index layer.

4. The photo-detection system according to claim 1, wherein the photodetector further includes:
   first microlenses each disposed on a corresponding one of the first photo-detection cells, and
   second microlenses each disposed on a corresponding one of the second photo-detection cells.

5. A photo-detection system comprising:
   a photo-detection apparatus; and
   an arithmetic circuit,
   the photo-detection apparatus including:
      a light-shielding film including light-transmitting regions and light-shielding regions,
      the light-transmitting regions and the light-shielding regions being alternately arranged in at least a first direction within a plane, an optically-coupled layer facing the light-shielding film, the optically-coupled layer including a grating which generates a propagating light that propagates in the first direction and a transmitting light that transmits the optically-coupled layer when incident light of a predetermined wavelength enters the light-transmitting regions, and a photodetector having an imaging area, the photodetector including first photo-detection cells and second photo-detection cells, the first photo-detection cells and the second photo-detection cells being arranged on the imaging area, each of the first photo-detection cells corresponding to at least one of the light-transmitting regions, each of the second photo-detection cells corresponding to at least one of the light-shielding regions, and the arithmetic circuit correcting each of first signals that are obtained from at least part of the first photo-detection cells by using two of the first signals that are obtained from two of the first photo-detection cells located closest in the first direction and a direction opposite to the first direction to each of the at least part of the first photo-detection cells, the arithmetic circuit correcting each of second signals that are obtained from at least part of the second photo-detection cells by using two of the second signals that are obtained from two of the second photo-detection cells located closest in the first direction and the direction opposite to the first direction to each of the at least part of the second photo-detection cells, the arithmetic circuit outputting, based on the first signals thus corrected and the second signals thus corrected, third signals each representing coherence of light having entered a position of each of the first and second photo-detection cells.

6. The photo-detection system according to claim 5, wherein the arithmetic circuit corrects each of the first signals by further using two of the first signals that are obtained from two of the first photo-detection cells located second closest in the first direction and the direction opposite to the first direction to each of the at least part of the first photo-detection cells, and the arithmetic circuit corrects each of the second signals by further using two of the second signals that are obtained from two of the second photo-detection cells located second closest in the first direction and the direction opposite to the first direction to each of the at least part of the second photo-detection cells.

7. The photo-detection system according to claim 5, wherein the arithmetic circuit generates, as the third signals corresponding to the at least part of the first photo-detection cells, signals that are obtained by an operation $P_1'/(P_0+P_1')$, $P_0/(P_0+P_1')$ or $P_1'/P_0$, and generates, as the third signals corresponding to the at least part of the second photo-detection cells, signals that are obtained by an operation $P_1/(P_0'+P_1)$, $P_0'/(P_0'+P_1)$ or $P_1/P_0'$, where $P_0$ is each of the first signals thus corrected, $P_1$ is each of the second signals thus corrected, $P_1'$ is an average value of two signals that are obtained from two of the second photo-detection cells which are adjacent to each of the at least part of the first photo-detection cells in the first direction and the direction opposite to the first direction, and $P_0'$ is an average value of two signals that are obtained from two of the first photo-detection cells which are adjacent to each of the at least part of the second photo-detection cells in the first direction and the direction opposite to the first direction.

8. The photo-detection system according to claim 5, wherein the optically-coupled layer further includes:

a first low-refractive-index layer, a first high-refractive-index layer disposed on the first low-refractive-index layer and including the grating, and a second low-refractive-index layer disposed on the first high-refractive-index layer, and the first high-refractive-index layer has a higher refractive index than the first low-refractive-index layer and the second low-refractive-index layer.

9. The photo-detection system according to claim 5, wherein the photodetector further includes:

first microlenses each disposed on a corresponding one of the first photo-detection cells, and second microlenses each disposed on a corresponding one of the second photo-detection cells.

* * * * *